(12) United States Patent
Stephenson et al.

(10) Patent No.: US 9,765,077 B2
(45) Date of Patent: Sep. 19, 2017

(54) SYNTHESIS OF DUOCARMYCIN ANALOGUES

(71) Applicant: University of East Anglia, Norwich (GB)

(72) Inventors: Michael J Stephenson, Norwich (GB); Lesley A Howell, Norwich (GB); Mark Searcey, Norwich (GB)

(73) Assignee: University of East Anglia, Norwich (GB)

( * ) Notice: Subject to any disclaimer, the term of this patent is extended or adjusted under 35 U.S.C. 154(b) by 0 days.

(21) Appl. No.: 14/725,252

(22) Filed: May 29, 2015

(65) Prior Publication Data

US 2016/0347753 A1    Dec. 1, 2016

(51) Int. Cl.
*C07D 487/04* (2006.01)
*C07D 471/04* (2006.01)

(52) U.S. Cl.
CPC ............................. *C07D 487/04* (2013.01)

(58) Field of Classification Search
CPC ........................... C07D 487/04; C07D 471/04
USPC ............................................. 548/433; 546/84
See application file for complete search history.

(56) References Cited

PUBLICATIONS

Stephenson, M., M. O'Connell, S. Collingwood, and M. Searcey "Utilisation of Fmoc solid phase chemistry as a novel approach to the generation of duocarmycin analogues" Poster, ACS Fall 2014 National Meeting (Aug. 10, 2014), San Francisco, CA.*
Okano, K., Tokuyama, H., and T. Fukuyama "Total Synthesis of (+)-Yatakemycin" Chem. Asian J. (2008), 3: pp. 296-309.*
Stephenson, M. J., et al., "Utilisation of Fmoc solid phase chemistry as a novel approach to the generstion of duocarmycin analogues" Poster, ACS Fall 2014 National Meeting, San Francisco, CA (Aug. 10, 2014).
Boger, D. L., et al., "Synthesis of CC-1065 and duocarmycin analogues via intramolecular aryl radical cyclization of a tethered vinyl chloride," *Tetrahedron Letters*, 39:2227-2230 (1998).
Hiroya, K., et al., "New synthetic method for indole-2-carboxylate and its application to the total synthesis of duocarmycin SA," *Organic Letters*, 6(17):2953-2956 (2004).
ISR of WO/2016/193709, Dec. 8, 2016, University of East Anglia.
Okano, Kentaro et al., "Total Synthesis of (+)-Yatakemycin", *J Am Chem Soc*,128 (22):7136-7137, Jun. 1, 2006.
Stephenson, Michael J. "Utilisation of Fmoc Solid Phase Chemistry as a Novel Approach to the Generation of Duocarmycin Analogues," *Division of Medicinal Chemistry Scientific Abstracts for the 248th National Meeting and Exposition*, Aug. 14, 2014 Abstract MEDI 198.
Tichenor, Mark S. et al., "Asymmetric Total Synthesis Of (+)- and Ent-(-)-Yatakemycin and Duocarmycin SA: Evaluation of Yatakemycin Key Partial Structures and Its Unnatural Enantiomer", *J Am Chem Soc*,128(49): 15683-15696 Dec. 1, 2006.
Tichenor Mark S. et al., "Systematic Exploration of the Structural Features of Yatakemycin Impacting DNA Alkylation and Biological Zctivity", *J Am Chem Soc* , 129(35): 10858-10869, Sep. 1, 2007.
Nagamura, Satoru et al., "Studies on Duocarmycin SA and Its Derivatives", *Bioorganic & Medicinal Chemistry*, 5(3): 623-630 Mar. 1, 1997.
Wolfe Amanda L., et al., "A Fundamental Relationship Between Hydrophobic Properties and Biological Activity for the Duocarmycin Class of DNA-Alkylating Antitumor Drugs: Hydrophobic-Binding-Driven Bonding", *J Med Chem*, 56(17): 6845-6857 Sep. 12, 2013.
Stephenson Michael J. et al., "Solid-Phase Synthesis of Duocarmycin Analogues and the Effect of C-Terminal Substitution on Biological Activity", *J Org Chem*, 80(19): 9454-9467, Oct. 2, 2015.

* cited by examiner

*Primary Examiner* — Matthew Coughlin
*Assistant Examiner* — Sagar Patel
(74) *Attorney, Agent, or Firm* — Antoinette G. Giugliano; AGG Intellectual Property Law

(57) ABSTRACT

A novel Fmoc protected duocarmycin subunit and utilization as a reagent in solid phase protein synthesis methodology. Also provided is a novel method of solid phase peptide synthesis, and in particular a method for the production of novel intermediates and novel monomeric and extended duocarmycin analogues having amino acid substituents.

12 Claims, 4 Drawing Sheets

Qualitative analysis for different resins used (see text). HBTU was used as the coupling reagent Qualitative analysis for different coupling reagents used (see text). 2-Cl-Trt was used as the resin

SYNTHESIS OF DUOCARMYCIN ANALOGUES

FIELD

The disclosure relates to a method of solid phase synthesis, and in particular a method for the production of duocarmycin analogues.

The disclosure further relates to a (+)-DSA subunit that is suitably protected for utilisation in solid phase methodology.

The disclosure further relates to novel duocarmycin analogues.

BACKGROUND

The duocarmycins are potent antitumour agents with potential in the development of antibody drug conjugates (ADCs) as well as being clinical candidates in their own right. The duocarmycin family of natural products incorporates the parent molecule duocarmycin SA (FIG. 1, (1)), several naturally occurring analogues and the extended and sandwiched compounds CC-10653 (FIG. 1, (2)) and yatakemycin (FIG. 1, (3)). The mode of action of these compounds, involving reversible alkylation of the N3 of adenine through shape dependant activation on binding to the minor groove of DNA, has been the subject of extensive investigation and has led to the design and synthesis of numerous analogues. Most recently, research has focussed on prodrugs that are reductively or oxidatively-activated or that carry glycosidic linkages. This desire to generate prodrug structures is due to the ultrapotent activity of the drug molecules.

One route into the design of new molecular entities with therapeutic potential whilst minimising cytotoxicity is via tumour cell targeting, rather than prodrug design. Antibody-drug conjugates, in which the antibody targets a highly cytotoxic molecule to the tumour site of action, have met with some recent success in the clinic.

SUMMARY OF THE INVENTION

We believe this is the first time the duocarmycin SA alkylation subunit, hereafter termed (+)-DSA, has been incorporated directly into solid phase peptide methodology.

In an embodiment there is provided a (+)-DSA subunit that is suitably protected for utilisation in solid phase methodology.

The racemic protected DSA subunit can be separated, if desired, by supercritical fluid chromatography (SFC) into the single enantiomers.

In another aspect of the invention, application of the (+)-DSA subunit to solid phase synthesis methodology gives a series of monomeric and extended duocarmycin analogues with amino acid substituents.

Single enantiomers of the DSA subunit may also be used in solid phase synthesis to give a series of monomeric and extended duocarmycin analogues with amino acid substituents.

New duocarmycin agents are herein made by incorporating the DSA subunit onto the solid phase with a peptide moiety at the C-terminus. The effect of the presence of the differing side chains at the C-terminus on DNA binding and biological activity was determined. The Applicants surprisingly discovered that substitutions at this position have a profound effect on the antiproliferative activity of the compounds. Presence of an ester results in cytotoxicity, whereas hydrolysis of the ester to give the free acid effectively removes all cytotoxic effects. Surprisingly, the presence of a free amino acid also affects antiproliferative activity. The combination of a free amino acid with an extended group on the N-terminus was surprisingly found to increase antiproliferative activity. However, incorporation of a terminal amine or amide has little effect on activity.

DETAILED DESCRIPTION OF THE INVENTION

The (+)-DSA Subunit for Fmoc-Chemistry

Figure 1:
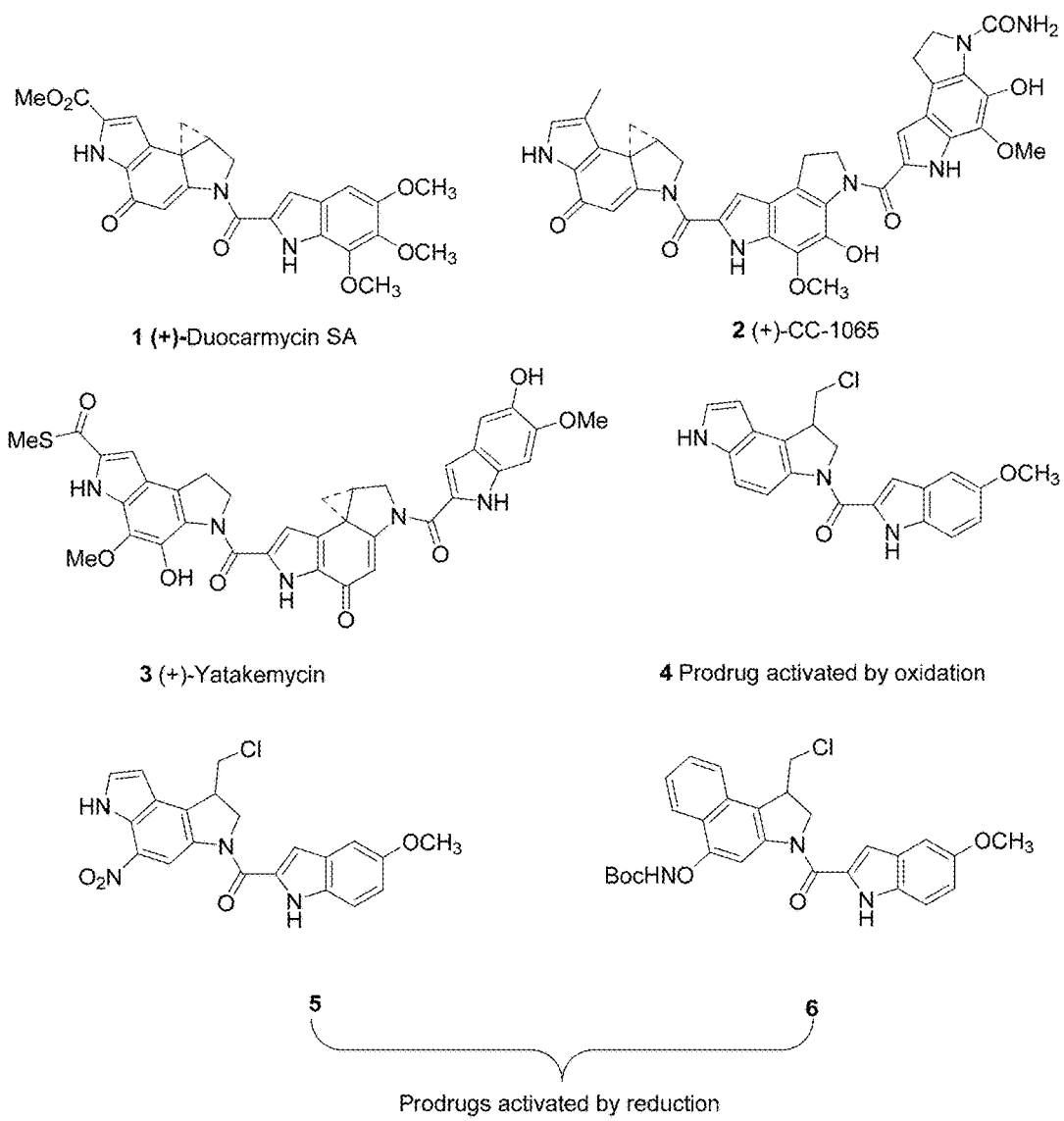
FIG. 1 is a figure of Duocarmycin SA and biooxidative and bioreductive prodrugs.

In a first embodiment there is a compound of general formula I

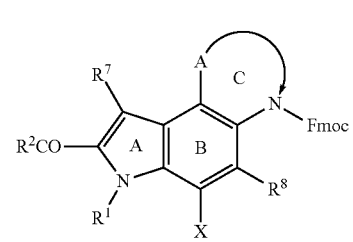

wherein
A is CH(CH$_2$Y) CH$_2$ or CH$_2$CH(Y)CH$_2$;
Y is a leaving group;
R$^1$ is H, C$_{1-6}$ alkyl or an amine-protecting group;
R$^2$ is OH, OR$^3$, SR$^{10}$, N(R$^4$)$_2$, or a carboxyl protecting group or a carboxylic acid activating group;

$R^3$ is $C_{1-6}$ alkyl, $C_{5-24}$ aryl, heteroaryl or $C_{1-6}$ substituted alkyl;

the or each $R^4$ is independently selected from H, $C_{1-6}$ alkyl, $C_{5-24}$ aryl, heteroaryl, $C_{1-6}$ substituted alkyl, C-terminal peptide of a solid phase peptide-synthetic substrate group optionally linked to a SPPS substrate, and $Ar^1$;

where $Ar^1$ is selected from

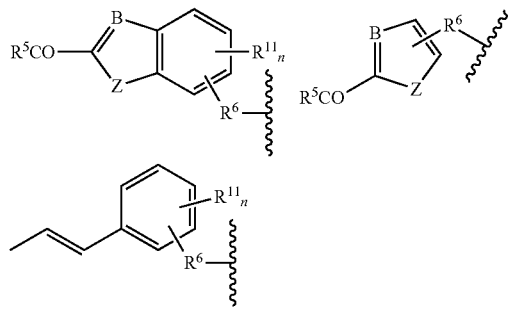

or two $R^4$'s together represent

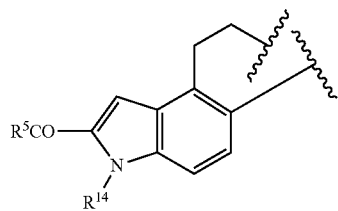

X is OH or $OR^9$;

$R^7$ and $R^8$ are independently selected from H, $C_{1-4}$ alkyl, OH, $C_{1-4}$ alkoxy, $C_{1-6}$ alkyl, CN, Cl, Br, I and $NO_2$;

the or each $R^5$ is OH, $OR^3$, $SR^{10}$, $N(R^6)_2$, or a carboxyl protecting group or a carboxylic acid activating group;

the or each $R^6$ is a bond, a $C_{1-6}$ alkanediyl, a $C_{6-24}$ arylene, a $C_{6-24}$ alkarylene, a heteroarylene or heteroaryl-alkylene;

Z is O, S, —CH═CH or $NR^{14}$;

B is N or CH;

the or each $R^{11}$ is independently selected from H, $C_{1-4}$ alkyl, OH, $C_{1-4}$ alkoxy, $C_{1-6}$ alkyl, CN, Cl, Br, I and $NO_2$;

n is 0-4;

$R^9$ is $C_{1-6}$ alkyl, $C_{5-24}$ aryl, heteroaryl, $C_{1-6}$ substituted alkyl or a phenol protecting group;

$R^{10}$ is H, $C_{1-6}$ alkyl, $C_{5-24}$ aryl, heteroaryl or $C_{1-6}$ substituted alkyl;

and $R^{14}$ is H, $C_{1-6}$ alkyl or an amine protecting group.

Preferably A is $CH(CH_2Y)$ $CH_2$.

The leaving group is the basis for the alkylating functionality of the duocarmycin core. In the invention the leaving group Y is, for instance, a group which has utility as a leaving group in nucleophilic substitution reactions. Suitable examples of such groups are $—OCOOR^{15}$, $—OCONHR^{16}$, Cl, Br, I, or $—OSOOR^{17}$, in which $R^{15}$, $R^{16}$ and $R^{17}$ are independently selected from $C_{1-4}$ alkyl, optionally substituted phenyl, $C_{7-12}$-aralkyl and optionally substituted heteroaryl. Preferably the leaving group is a halogen atom, most preferably chlorine.

In the invention, heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, phenyl, isoxazolyl, and oxazolyl. Most preferably the heteroaryl group is pyridinyl, pyrrolyl or pyridazinyl. Most preferably it is pyridinyl.

Fmoc serves as the amine protecting group of the C ring.

Preferably $R^1$ is H or an amine protecting group. Most preferably $R^1$ is H.

Examples of amine protecting groups, for instance protecting the nitrogen atom of the A ring, are benzyl, benzyloxycarbonyl, tertiary butyloxycarbonyl (BOC) and 2-[biphenylyl-(4)]-propyl-2-oxycarbonyl. A particularly preferred amine protecting group protecting the nitrogen atom of the A ring is BOC.

Where more than one such amine group is protected in the molecule, the protecting groups may be the same or different. However, the amine protecting group protecting the nitrogen atom of the A ring is other than Fmoc in order that the specified Fmoc group of the novel compound can be selectively de-protected whilst the amine protecting group is retained.

$R^2$ is preferably OH or a carboxyl protecting group or a carboxylic acid activating group. Most preferably $R^2$ is OH.

Most preferably X is $OR^9$. Preferably $R^9$ is $C_{1-6}$ alkyl or $C_{5-24}$ aryl. More preferably $R^9$ is $C_{5-24}$ aryl. Most preferably $R^9$ is benzyl.

Preferably $R^7$ and $R^8$ are independently selected from H, $C_{1-4}$ alkyl and OH. Most preferably $R^7$ and $R^8$ are both H.

Optional substituents in alkyl groups are halogen, hydroxyl, $—NH_2$, $—NO_2$—, —CN, —COOH, or any other substituent known in the art. Preferably, the optional substituents in alkyl groups are halogen, hydroxyl or $—NH_2$. Most preferably the optional substitutents are halogens. Preferably the alkyl groups are unsubstituted.

Suitable carboxyl protecting groups and carboxylic acid activating groups are known in the art. Methyl esters, benzyl esters, tert-butyl esters, silyl esters, orthoesters or oxazoline may be used as the carboxyl protecting group. Preferably methyl esters, and benzyl esters are used. More preferably t-Butyl is used. Suitable carboxylic acid activating groups include carbodiimides, triazolols and uronium salts. Preferably the carboxylic acid activating groups is a carbodiimide. Preferably the uronium salt is HBTU.

In the invention, heteroarylene groups include but are not limited to a bivalent aromatic 5-8 membered monocyclic, 8-12 membered bicyclic, or 11-14 membered tricyclic ring system having one or more heteroatoms such as O, N, S or Se. Preferably the heteroarylene group includes a bivalent aromatic 5-8 membered monocyclic ring system having one or more heteroatoms such as O, N, S or Se.

In the invention heteroaryl-alkylene groups include, but are not limited to, an optionally substituted heteroaryl linked via $(CH_2)_n$ wherein n=1-15, preferably where n=1-6.

In the invention any substituted or unsubstituted alkanediyl group may be used. Preferably the alkanediyl group comprises 2 to 10 carbon atoms. More preferably the alkanediyl group is selected from —CH—, $—CHCH_2—$, $—CH_2CH_2CH_2—$ and $—CH(CH_3)CH_2—$.

In the invention any $C_{6-24}$ arylene group may be used. The $C_{6-24}$ arylene group links to the two attached parts of the molecule via ring atoms. Preferred arylene groups herein are phenylene and naphthylene. Most preferably the arylene group used is phenylene.

In the invention any $C_{6-24}$ alkarylene group may be used. The $C_{6-24}$ alkarylene groups have one linkage to the aliphatic group and one to an aromatic ring atom. Preferred $C_{6-24}$ alkarylene groups include, but are not limited to tolylene and xylylene. Most preferably tolylene is used.

In the invention, amino acids are preferably naturally occurring alpha-amino acids.

The compounds of the first embodiment are useful as starting materials for use in solid phase synthetic methods. The starting materials may be provided with free or activated carboxylic acids as the $R^2CO$ moiety, suitable for linkage to an amine group on a solid phase substrate, for instance having an amino acyl unit attached, or a peptidyl group, conjugated to a substrate. In such an embodiment $R^2$ is OH or an activated carboxylic acid group.

The compound formed by reaction of such a starting material is itself an embodiment of the invention.

The solid phase peptide-synthetic substrate group may be any substrate group bonded to the SPPS substrate. The solid phase peptide-synthetic substrate group may be left over on the synthesised peptide once the peptide has been cleaved from the resin and it would be clear to the skilled person which groups this could be.

The SPPS substrate may be any commercially available resin for peptide synthesis including Wang resin, Rink amide resin and chlorotrityl resin. Preferably a chlorotrityl resin is used.

The product of the reaction onto a solid-phase peptide synthesis (SPPS) substrate will have $R^2$ as $N(R^4)_2$ where one of the $R^4$ groups is H and the other is an amino acid residue of the SPPS substrate.

Any linker group between the SPPS substrate and the CO joined to $R^2$ may be selected for its functionality, for instance its cleavability during synthesis or after administration or to provide binding or conjugation functionality.

Most preferably, compound I is of the formula:

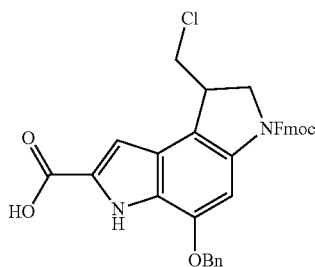

Synthesis of the Compound for Fmoc-Chemistry

The compound of the invention, for instance where $R^2$ is OH or a carboxylic acid protecting group, is usually formed by reaction of the FMOC group onto the corresponding free amine. Where the amine starting material has other amine groups, conditions must be chosen that are regioselective for the amine substituent on the respective ring. For instance, where the A ring is a dihydro-indole, reaction with Fmoc-Cl preferentially takes place under basic conditions.

The amine starting material is a known class of compounds. They may be formed with any secondary amine groups in protected form, for instance as a BOC-protected group, with preliminary deprotection of the protecting group followed by Fmoc protection as described above.

In a preferred embodiment an acidic reaction is used for the removal of the BOC groups, followed by a basic reaction with Fmoc-Cl to form the product.

Stereoselective routes to the target compound can also be performed using methods known in the art.

Separation of Enantiomers Using Supercritical Fluid Chromatography

The application of supercritical fluid chromatography for the chiral resolution of racemic mixtures is well established.

Supercritical fluids combine the density, and dissolution character of a liquid, with a viscosity, and diffusion behaviour more comparable to a gas. The low viscosity improves mass-transfer kinetics, and permits the use of fast flow rates with high acuity columns. These properties make them ideal mobile phases, and allow for highly efficient separations. As such this technique is particularly attractive for preparative scale work, and was employed for the isolation of each enantiomer of the (+)-DSA subunit.

Analytical supercritical fluid chromatography suggested the loss of Cl as opposed to racemisation. NMR analysis showed no evidence of this impurity, with the $H^1$ NMR of both enantiomers being identical to that of the racemate, with the exception of a small amount of residue IPA.

Peaks were assigned as the natural enantiomer based on the sign of specific rotation matching that of the well characterised seco-Boc-DSA derivative Application of Fmoc-Protected Compound I to Solid Phase Peptide Synthesis.

The Fmoc protected compounds of the present invention have been found to have very useful applications, particularly in the field of solid phase peptide synthesis.

Therefore, in a second aspect of the invention there is provided a method of synthesising an amide compound by the following steps:

a) deprotecting a compound of general formula I by removing the FMOC group to leave a free secondary amine group-containing intermediate

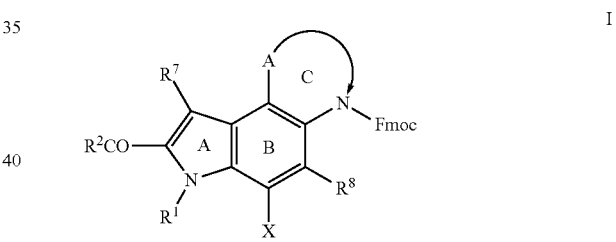

wherein
A is $CH(CH_2Y) CH_2$ or $CH_2CH(Y)CH_2$;
Y is a leaving group;
$R^1$ is H, $C_{1-6}$ alkyl, or an amine protecting group;
$R^2$ is OH, $OR^3$, $SR^{10}$, $N(R^4)_2$, or a carboxyl protecting group or a carboxylic acid activating group;
$R^3$ is $C_{1-6}$ alkyl, $C_{5-24}$ aryl, heteroaryl, $C_{1-6}$ substituted alkyl;
the or each $R^4$ is independently selected from H, $C_{1-6}$ alkyl, $C_{5-24}$ aryl, heteroaryl, $C_{1-6}$ substituted alkyl, the C-terminal residue of an amino acid, C-terminal peptide of a solid phase peptide-synthetic substrate group optionally linked to a SPPS substrate, and $Ar^1$;
where $Ar^1$ is selected from

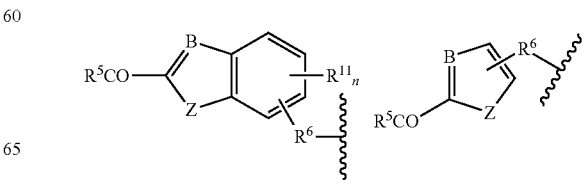

-continued

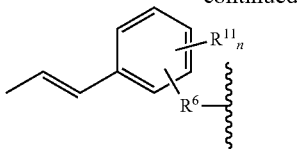

or two $R^4$'s together represent

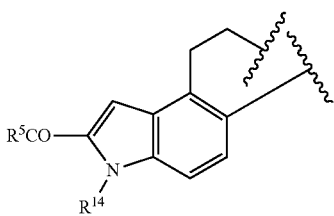

X is OH or $OR^9$;
$R^7$ and $R^8$ are independently selected from H, $C_{1-4}$ alkyl, OH, $C_{1-4}$ alkoxy, $C_{1-6}$ alkyl, CN, Cl, Br, I and $NO_2$;
the or each $R^5$ is OH, $OR^3$, $SR^{10}$, $N(R^6)_2$, or a carboxyl protecting group or a carboxylic acid activating group;
the or each $R^6$ is a bond, a $C_{1-6}$ alkanediyl, a $C_{6-24}$ arylene, a $C_{6-24}$ alkarylene, a heteroarylene or heteroaryl-alkylene;
Z is O, S, —CH═CH or $NR^{14}$;
B is N or CH;
the or each $R^{11}$ is independently selected from H, $C_{1-4}$ alkyl, OH, $C_{1-4}$ alkoxy, $C_{1-6}$ alkyl, CN, Cl, Br, I and $NO_2$;
n is 0-4;
$R^9$ is $C_{1-6}$ alkyl, $C_{5-24}$ aryl, heteroaryl, $C_{1-6}$ substituted alkyl or a phenol protecting group;
$R^{10}$ is H, $C_{1-6}$ alkyl, $C_{5-24}$ aryl, heteroaryl or $C_{1-6}$ substituted alkyl; and $R^{14}$ is H, $C_{1-6}$ alkyl or an amine protecting group;
b) contacting the secondary amine group containing intermediate with a carboxylate reagent of the formula II $R^{13}COR^{12}$  II where $R^{12}$ is OH or a carboxylic acid activating group;
$R^{13}$ is $C_{1-6}$ alkyl, $C_{5-24}$ aryl, heteroaryl or $C_{1-6}$ substituted alkyl, any of which may be substituted by a targeting ligand or a cytotoxic moiety or $Ar^2$ or $R^{13}$ is

FMOC—NH—CH($R^{18}$)— where $R^{18}$ is the side chain of a natural or non-natural alpha amino acid; a targeting ligand or a cytotoxic moiety;
$Ar^2$ is selected from:

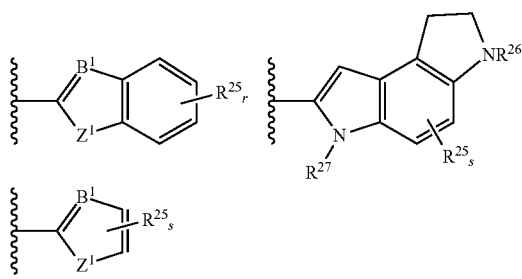

$Z^1$ is O, S, —CH═CH— or $NR^{27}$;
$B^1$ is N or CH;
s is 0, 1 or 2;

r is 0-4;
$R^{26}$ is selected from H, $CONH_2$, acyl, FMOC, $C_{1-6}$ alkyl, $C_{5-24}$ aryl, heteroaryl, $C_{1-6}$ substituted alkyl, C-terminal peptide and $Ar^2$; and
the or each $R^{25}$ is independently selected from $C_{1-6}$ alkyl, OH, $C_{1-6}$ alkoxy, $C_{1-6}$ alkylthio, CN, Cl, Br, I and $NO_2$ and —$R^{29}NHCOR^{28}$;
$R^{29}$ is a bond, a $C_{1-6}$ alkanediyl, a $C_{6-24}$ arylene, a $C_{6-24}$ alkarylene, a heteroarylene or heteroaryl-alkylene;
$R^{28}$ is $C_{1-6}$ alkyl, $C_{6-24}$ aryl, $C_{5-24}$ aralkyl, heteroaryl or $C_{1-6}$ substituted alkyl;
$R^{27}$ is $C_{1-6}$ alkyl or BOC
to form the said amide compound.
In a preferred embodiment, $R^{13}$ is $Ar^2$ and $Ar^2$ is a group of formula:

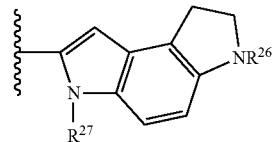

wherein $R^{27}$ is BOC and $R^{26}$ is FMOC.
Thus in this embodiment a DNA-binding subunit is linked to the secondary amine group.
In an alternative embodiment, $R^{13}$ is $Ar^2$ and $Ar^2$ is a group of formula:

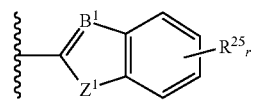

wherein r is 1-3 and the or each $R^{25}$ is independently selected from OH, $C_{1-6}$ alkyl, $C_{1-6}$ alkoxy and $C_{1-6}$ alkylthio. Preferably $R^{25}$ is independently selected from methoxy or hydroxy.
In an even preferred embodiment, $R^{13}$ is FMOC—NH—CH($R^{18}$) where $R^{18}$ is the side chain of a natural alpha amino acid.
A further embodiment of the process of the invention comprises the step of removing the second FMOC group of a product amide to leave a free amine group.
Optionally a further step b) as defined above is carried out with a second carboxylate reagent of formula II wherein $R^{13}$ is FMOC NH—CH($R^{18}$)— where $R^{18}$ is the side chain of a natural or non-natural alpha amino acid.
In this preferred embodiment of the invention, the compound of formula I has an $R^2$ group that is $N(R^4)_2$, where one of the groups $R^4$ is the C-terminal residue of an amino acid, a C-terminal peptidyl group or a solid phase peptide synthetic substrate linking group linked to SPPS-substrate. Where $R^4$ is a linking group linked to SPPS substrate the amide bond formation is a step of solid phase peptide synthesis.
In an alternative embodiment of the process of the invention, there are multiple cycles of step b) as described above for adding individual amino acids and/or cytotoxic moieties until the desired protein/active moiety is obtained. For example, this may comprise the step of removing the second FMOC group of a product amide to leave a free amine group, and optionally carrying out a further step b) as defined above with a second carboxylate reagent of formula II wherein $R^{13}$ is an alkyl or aryl group substituted by a targeting ligand or a cytotoxic moiety.

In a further preferred embodiment, preliminary steps of synthesising the compound of formula I comprise reacting a compound of general formula III

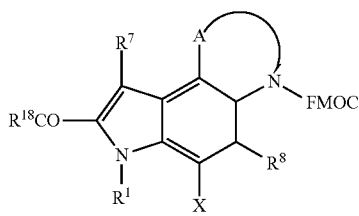

III wherein A is $CH(CH_2Y)$ $CH_2$ or $CH_2CH(Y)CH_2$,
$R^1$ is H, $C_{1-6}$ alkyl, or an amine protecting group;
$R^7$ and $R^8$ are independently selected from H, $C_{1-4}$ alkyl, OH, $C_{1-4}$ alkoxy, $C_{1-6}$ alkyl, CN, Cl, Br, I and $NO_2$,
X is OH, or $OR^9$,
$R^9$ is $C_{1-6}$ alkyl, $C_{5-24}$ aryl, heteroaryl or $C_{1-6}$ substituted alkyl;
and $R^{18}$ is OH or a carboxylic acid activating group with a compound of formula IV $$R^{20}NHR^{19} \quad [IV]$$

where $R^{19}$ is H or $C_{1-6}$ alkyl,
and $R^{20}$ is $C_{1-6}$ alkyl, $C_{5-24}$ aryl, heteroaryl, $C_{1-6}$ substituted alkyl or $CH(R^{18})$ $COR^{21}$ where $R^{18}$ is the side chain of a natural or non-natural amino acid and $R^{21}$ is a carboxylic acid protecting group or a C-terminal peptidyl moiety or a linker group of a SPPS substrate;
or $R^{19}$ and $R^{20}$ are linked to form a saturated or unsaturated 5 or 6 membered heterocyclic ring.

In a further preferred embodiment, $R^{20}$ of formula IV is $CH(R^{18})COR^{21}$ wherein $R^{21}$ is a linker group of a SPPS substrate. This preliminary step is a SPPS amide bond forming step. The SPPS substrate may be any commercially available resin for peptide synthesis including Wang resin, Rink amide resin and chlorotrityl resin. Preferably a chlorotrityl resin is used.

In a particularly preferred embodiment, $R^{21}$ is a peptidyl linker linked to a resin, preferably a chlorotrityl resin. $R^{21}$ can be any amino acid or peptide sequence.

The SPPS-substrate bound compounds may be cleaved using standard SPPS-based techniques to produce amide compounds in solution form for subsequent recovery and use.

The amide compounds produced via the methods of the invention are of particular use, for instance to link to targeting proteins such as antibodies or other drug delivery molecules such as polymers, carbohydrates, oligo and polysaccharides and so on. Peptide molecules may be synthesised directly on the SPPS substrate, before or after the compound of formula I is conjugated to carboxylic reagent II. Alternatively, a protein based molecule such as an antibody may be pre-formed and conjugated before or after cleavage from the SPPS substrate.

The amino-acyl-conjugated amide compounds formed in the method of the invention are new. These compounds, formed from the method of the invention, encompass intermediates as well as end products, and encompass compounds still linked to the resin or not linked to resin and useful for conjugating to a binding group. Therefore, in a further aspect of the invention, compounds of general formula V are also herein disclosed. The Applicants have found that compounds of formula V display DNA alkylation activity, with some having significantly increased DNA alkylation activity compared with Duocarmycin SA itself, and thus may have therapeutic activity:

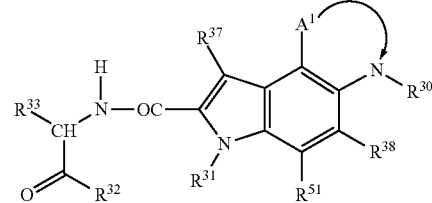

V wherein
$A^1$ is $CH(CH_2Y^1)$ $CH_2$ or $CH_2CH(Y^1)CH_2$;
$Y^1$ is a leaving group;
$R^{31}$ is H, $C_{1-6}$ alkyl or an amine protecting group;
$R^{32}$ is OH, a carboxyl protecting group or $NHR^{34}$;
$R^{33}$ is selected from H, $C_{1-6}$ alkyl, $C_{5-24}$ aryl, heteroaryl and/or the side chain of a natural α-amino acid;
$R^{34}$ is the residue of an amino acid or peptidyl group;
$R^{37}$ and $R^{38}$ are independently selected from H, $C_{1-6}$ alkyl, OH, $C_{1-4}$ alkoxy, CN. Cl, Br, I and $NO_2$;
$R^{51}$ is OH or O bonded to a phenol protecting group;

Examples of phenol protecting groups include Triisopropylsilyl ether (TIPS), tert-Butyldimethylsilyl ether (TBS, TBDMS), methyl ether, Benzyl ether (Bn), methoxymethyl acetal (MOM) and 2-(Trimethylsilyl)ethoxy]methyl acetal (SEM).

$R^{30}$ is H, $C_{1-6}$ alkyl, an amine protecting group, or $Ar^3$;
$Ar^3$ is selected from:

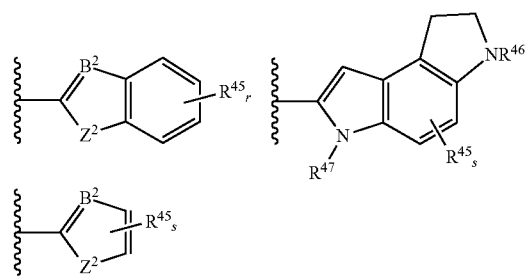

$Z^2$ is O, S, —CH=CH— or $NR^{47}$;
$B^2$ is N or CH;
s is 0, 1 or 2;
r is 0-4;
the or each $R^{45}$ is independently selected from $C_{1-6}$ alkyl, OH, $C_{1-6}$ alkoxy, $C_{1-6}$ alkylthio, CN, Cl, Br, I and $NO_2$ and —$R^{49}NHCOR^{48}$. Preferably $R^{25}$ is independently selected from methoxy or hydroxy.
$R^{46}$ is selected from H, CON $H_2$, acyl, FMOC, $C_{1-6}$ alkyl, $C_{5-24}$ aryl, heteroaryl, $C_{1-6}$ substituted alkyl, C-terminal peptide and $Ar^3$; and
$R^{47}$ is H, $C_{1-6}$ alkyl or BOC;
$R^{48}$ is $C_{1-6}$ alkyl, $C_{6-24}$ aryl, $C_{5-24}$ aralkyl, $C_{6-24}$ alkaryl, heteroaryl or $C_{1-6}$ substituted alkyl;
$R^{49}$ is a bond, a $C_{1-6}$ alkanediyl, a $C_{6-24}$ arylene, a $C_{6-24}$ alkarylene, a heteroarylene or heteroaryl-alkylene;

Preferably $A^1$ is $CH(CH_2Y) CH_2$.
Preferably $Y^1$ is a halogen atom, most preferably chlorine.
Preferably $R^{31}$, $R^{37}$, and $R^{38}$ are independently H.
Preferably $R^{30}$ is acetyl. Alternatively, $R^{30}$ is preferably:

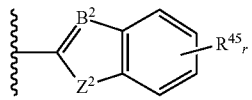

Preferably $B^2$ is CH, preferably $Z^2$ is $NR^{47}$, preferably $R^{47}$ is H, preferably $R^{45}$ is methoxy and r is 1.
In the final product, $R^{51}$ is likely to be OH.
Preferably $R^{32}$ is OH
Preferably $R^{33}$ is the side chain of a natural α-amino acid. This may be the side chain of any natural α-amino acid. Preferably the side chain is of α alanine, phenylalanine or serine. Most preferably $R^{33}$ is the side chain of serine. These show relatively high levels of antiproliferative activity.

The combination of a free amino acid with an extended group on the N-terminus is surprisingly found to increase antiproliferative activity compared to simple alkylating agents of formula V.

Additionally, compounds can be made for instance wherein a polypeptide or oligopeptide may be bonded to the C ring.

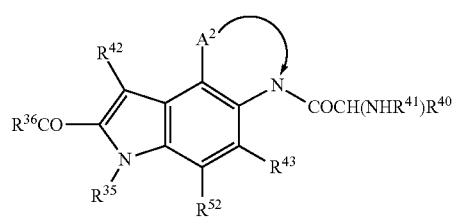

VI wherein
$A^2$ is $CH(CH_2Y) CH_2$ or $CH_2CH(Y)CH_2$;
Y is a leaving group;
$R^1$ is H, $C_{1-6}$ alkyl, FMOC or BOC;
$R^{36}$ is OH, $OR^{53}$, $SR^{50}$, $N(R^{44})_2$, or a carboxyl protecting group or a carboxylic acid activating group;
$R^{53}$ is $C_{1-6}$ alkyl, $C_{5-24}$ aryl, heteroaryl, or $C_{1-6}$ substituted alkyl;
the or each $R^{44}$ is independently selected from H, $C_{1-6}$ alkyl, $C_{5-24}$ aryl, heteroaryl, $C_{1-6}$ substituted alkyl; the C-terminal residue of an amino acid, and a C-terminal peptide linker of a solid phase peptide-synthetic substrate group optionally linked to a SPPS substrate;
$R^{42}$ and $R^{43}$ are independently selected from H, $C_{1-4}$ alkyl, OH, $C_{1-4}$ alkoxy, $C_{1-6}$ alkyl, CN, Cl, Br, I and $NO_2$;
$R^{50}$ is H, $C_{1-6}$ alkyl, $C_{5-24}$ aryl, heteroaryl, or $C_{1-6}$ substituted alkyl;
$R^{41}$ is H, an amine protecting group, $COCH(NHR^{41})R^{40}$, or CO peptidyl;
$R^{40}$ is H, $C_{1-6}$ alkyl, $C_{5-24}$ aryl, heteroaryl or the side chain of an alpha amino acid.
$R^{52}$ is OH or O bonded to a phenol protecting group. Preferably $R^{52}$ is O bonded to a phenol protecting group.
Examples of phenol protecting groups include Triisopropylsilyl ether (TIPS), tert-Butyldimethylsilyl ether (TBS, TBDMS), methyl ether, Benzyl ether (Bn), methoxymethyl acetal (MOM) and 2-(Trimethylsilyl)ethoxy]methyl acetal (SEM).

Previously, the enediyne antibiotic calicheamicin was conjugated to an anti-CD33 antibody to generate the clinically utilised agent gemtuzumab for the treatment of acute myelogenous leukemia (AML). Although this was subsequently withdrawn due to toxicity problems, it paved the way for brentuximab vedotin and trastuzumab emtansine, which are used in the treatment of Hodgkins lymphoma and breast cancer, respectively. Key to the design of antibody drug conjugates is the linker between the cytotoxic drug and the antibody. In gemtuzumab, the linker was cleaved under the acidic conditions that are formed in the endosomal compartment when the antibody is internalised in the cell. Brentuximab utilises a cathepsin cleavable linker to the antimitotic agent monomethylauristatin E. Trastuzumab emtansine contains a non-cleavable linker, such that as the protein is degraded in the environment of the endosome, the small molecule is released with the linker and a lysine residue still attached, nevertheless still exerting a cytotoxic effect. These latter two approaches require the attachment of the warhead molecule to the antibody through a peptidic linker. The method of the present invention provides a method of attaching a molecule to an antibody via a novel direct synthesis.

EXEMPLIFICATION

The invention is further described with reference to the following Example(s):

Example 1: Synthesis of the (+)-DSA Subunit for Fmoc-Chemistry

Synthesis started with 50 g commercially available 2-hydroxy-4-nitroaniline which was protected as the benzyl ether using BnBr, $K_2CO_3$ and DMF at room temperature. This was regioselectiviely iodinated using NIS and catalytic acid to give the iodo compound. Methods of synthesising duocarmycin are known in the art that employ a Negishi coupling and concomitant cyclization to afford the required indole. A similar Negishi coupling was employed, using $ZnBr_2$, $Pd(PPh_3)_2Cl_2$, DIPEA, methyl propiolate and DMF at 66° C., using $N_2$, to couple methyl propiolate. Subsequent ring closure to the indole was achieved as a separate step using tetrabutylammonium fluoride.

The indole was immediately protected. The protection step was carried out using $Boc_2O$, DMAP and $CH_2Cl_2$ to yield the pure protected indole after purification by flash column chromatography. The rest of the synthesis to the di-protected indole followed published methodology to introduce the dihydropyrrole ring structure.

Hydrolysis of the ester was followed by removal of both Boc-protecting groups, from the indole nitrogen and the secondary amine. Treatment of the resulting amino acid with Fmoc-Cl under basic conditions generates Fmoc-protected DSA, with a free nitrogen at the indole N-position and Fmoc protection on the secondary amine.

The synthesis of one compound according to general formula I of the invention is carried out according to the following reaction scheme:

Reaction scheme 1:

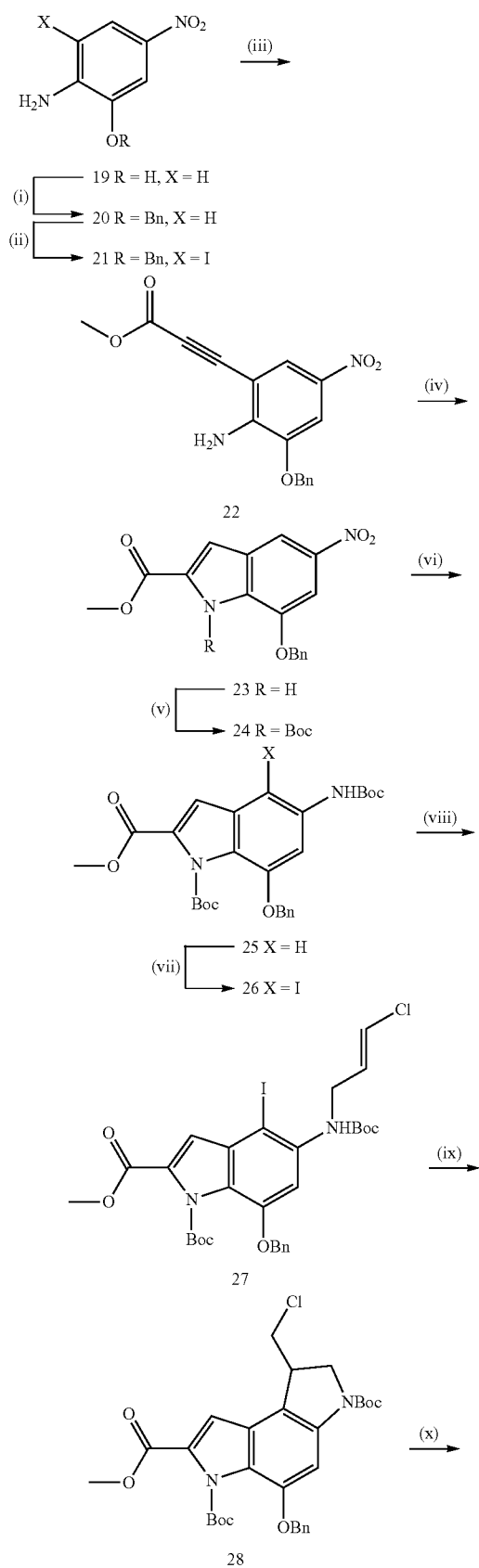

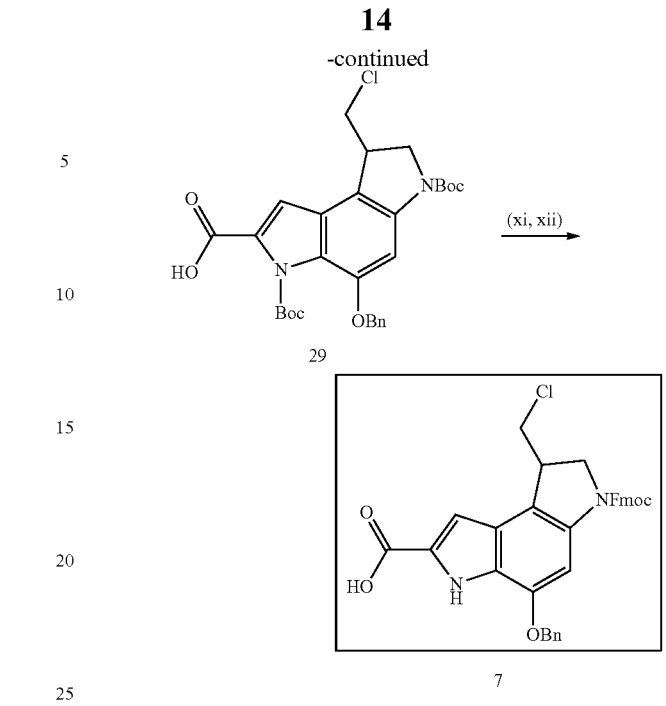

To manufacture compound (20): BnBr (21 mL, 178 mmol) was added dropwise to a stirring suspension of 2-amino-5-nitrophenol (25 g, 162 mmol) and $K_2CO_3$ (49.3 g, 357 mmol) in DMF (250 mL) at room temperature. After 20 hours, the reaction mixture was poured over crushed ice. The precipitate was collected by filtration and triturated with cold water prior to drying at 40° C. under vacuum overnight. The reaction was repeated and the two batches combined to afford 78.05 g of 20 as yellow/brown solid (98.5% average yield over the 2 batches).

$^1$H NMR (CDCl$_3$, 400 MHz) δ 7.83 (1H, dd, J=2.4, 8.7), 7.77 (1H, d, J=2.4), 7.37-7.46 (5H, m), 6.66 (1H, d, J=8.7), 5.15 (2H, s), 4.60 (2H, brs). $^{13}$C NMR (CDCl$_3$, 100 MHz) δ 144.6, 143.6, 138.7, 135.9, 128.9, 128.7, 128.0, 119.5, 112.1, 107.4, 71.0. IR (neat) v$_{max}$ 3483, 3359, 3225, 3188, 3075, 2939, 2876, 1622, 1579, 1519, 1480, 1455, 1386, 1282, 1222, 1176, 1091, 1007, 950, 914, 870, 853, 818, 797, 755, 744, 727, 697, 643, 623 cm$^{-1}$. HRMS (ES+) calculated for $C_{13}H_{13}N_2O_3$ (M+H)$^+$ 245.0921 found 245.0923.

To manufacture compound (21): $H_2SO_4$ (800 μL, 15.15 mmol) was added to a stirring solution of 20 (37 g, 151 mmol) in DMF (555 mL), followed by portionwise addition of NIS (51.1 g, 227 mmol) at room temperature. After 4 hours, the reaction mixture was poured over crushed ice. The precipitate was collected by filtration and triturated with cold water, followed by cold hexane, prior to drying at 40° C. under vacuum overnight. The reaction was repeated with 39.1 g of 21 and the two batches combined to afford 105.65 g as a bright yellow solid (91.5% average yield over the 2 batches). $^1$H NMR (CDCl$_3$, 400 MHz) δ 8.29 (1H, d, J=2.3), 7.74 (1H, d, J=2.3), 7.38-7.44 (5H, m) 5.16 (2H, s), 5.02 (2H brs). $^{13}$C NMR (CDCl$_3$, 100 MHz) δ 144.1, 143.3, 138.9, 135.4, 129.0, 128.9, 128.3, 128.1, 106.7, 178.5, 71.5. IR (neat) v$_{max}$ 3476, 3379, 3359, 3091, 3056, 3030, 2357, 2333, 1602, 1568, 1497, 1451, 1425, 1386, 1282, 1237, 1099, 1037, 1025, 869, 849, 819, 740, 726, 692 cm$^{-1}$. HRMS (ES+) calculated for $C_{13}H_{12}IN_2O_3$ (M+H)$^+$ 370.9887 found 370.9890.

To manufacture compound (22): 21 (40.8 g, 110 mmol) was dissolved in anhydrous DMF (1225 mL). The resulting solution was degassed with a stream of $N_2$ for 30 mins prior to addition of methyl propiolate (37.1 mL, 441 mmol), $Pd(PPh_3)_2Cl_2$ (3.87 g, 5.51 mmol), $ZnBr_2$ (99 g, 441 mmol), and DIPEA (77 ml, 441 mmol) at room temperature. The reaction mixture was then heated to 66° C. and stirred overnight under $N_2$. After cooling to room temperature the reaction was poured over crushed ice, and the resulting chocolate colour precipitate collected by filtration. The reaction was repeated with 51 g of 21, and the precipitates were combined prior to adsorption on to 250 g of silica. Elution through a 1 Kg silica plug with 50% ethyl acetate and hexane afforded 62 g of 22 as an orange solid (77% yield). $^1$H NMR ($CDCl_3$, 400 MHz) δ 8.06 (1H, d, J=2.4), 7.76 (1H, d, J=2.4), 7.38-7.45 (5H, m), 5.32 (2H, brs), 5.17 (2H, s), 3.86 (3H, s). $^{13}$C NMR ($CDCl_3$, 100 MHz) δ 154.1, 146.7, 144.5, 137.8, 135.2, 129.1, 129.0, 128.1, 123.0, 108.3, 101.0, 87.1, 81.1, 71.5, 53.1. IR (neat) $v_{max}$ 3499, 3391, 3351, 3087, 3063, 3030, 2951, 2204, 1698, 1611, 1455, 1430, 1393, 1325, 1299, 1237, 1215, 1148, 1093, 1040, 1028, 1001, 886, 859, 755, 740, 731, 694, 657, 612 $cm^{-1}$. HRMS (ES+) calculated for $C_{17}H_{15}N_2O_5$ $(M+H)^+$ 327.0975 found 327.0979.

To manufacture compound (24): 22 (60 g, 184 mmol) in anhydrous THF (858 mL) was treated with 1M TBAF in THF solution (368 mL, 368 mmol) and refluxed at 66° C. for 1 hour. After cooling to room temperature the THF was removed by rotary evaporation under reduced pressure. The residue was dissolved in ethyl acetate (1000 mL) and washed 3 times with water (1000 mL). Concentration of the ethyl acetate followed by co-evaporation of the residue with DCM afforded crude product as a dark purple foam. The foam was dissolved in DCM (1000 mL) and treated with $Boc_2O$ (80 g, 368 mmol), and DMAP (22.46 g, 184 mmol) at room temperature for 1.5 hours. Removal of the DCM gave a dark foam which was purified by silica gel chromatography using an Isco automated flash chromatography system. The crude was dry loaded on to a 1.5 kg pre-packed silica column adsorbed on to 200 g of silica. A linear gradient of 0 to 30% ethyl acetate in hexane was run over 23 column volumes and then held at 30% ethyl acetate until complete elution of the product. Removal of the solvent afford 31 g of 24 as an orange solid (39% yield of 2 steps). $^1$H NMR ($CDCl_3$, 400 MHz) δ 8.26 (1H, d, J=1.9), 7.67 (1H, d, J=1.9), 7.49-7.45 (2H, m), 7.41-7.34 (3H, m), 7.33 (1H, s) 5.33 (2H, s), 3.94 (3H, s), 1.47 (9H, s). $^{13}$C NMR ($CDCl_3$, 100 MHz) δ 160.5, 149.3, 145.6, 143.6, 135.2, 130.2, 128.9, 128.7, 128.2, 126.4, 112.7, 112.5, 102.2, 86.5, 71.3, 52.5, 27.9, 27.3. IR (neat) $v_{max}$ 3127, 3099, 3050, 2981, 2949, 1765, 1722, 1586, 1512, 1437, 1388, 1372, 1325, 1252, 1223, 1151, 1115, 1073, 982, 875, 840, 822, 801, 778, 766, 742, 729, 697, 606 $cm^{-1}$. HRMS (ES+) calculated for $C_{22}H_{23}N_2O_7$ $(M+H)^+$ 427.1500 found 427.1499.

To manufacture compound (26): 24 (15 g, 35.2 mmol) was dissolved in THF (293 ml) and treated with zinc powder (34.5 g, 528 mmol), $NH_4Cl$ (18.82 g, 352 mmol), $Boc_2O$ (23.03 g, 106 mmol), DMAP (430 mg, 3.52 mmol), and water (58.6 mL). The resulting suspension was stirred vigorously at room temperature overnight. After removal of the zinc by filtration, the THF was evaporated and the residue taken up in ether (500 mL). The ether was washed 3 times with water (250 mL) and died over $MgSO_4$. Co-evaporation with DCM gave crude 25 as a light brown foam. The reaction was repeated on the same scale and the crudes combined and dissolved in DMF (352 mL). $H_2SO_4$ (0.375 mL, 7.04 mmol) was added followed by portionwise addition of NIS (23.75 g, 106 mmol) at room temperature. After 3 hours the reaction was diluted with $Et_2O$ (1000 mL), and washed once with 50% saturated brine in water (1000 mL), twice with water (1000 mL), and once with saturated brine (1000 mL). The first wash was back extracted 3 times with $Et_2O$ (500 mL), which was subsequently combined and washed twice with saturated brine (1000 mL). All the $Et_2O$ was combined and concentrated to give a dark red foam which was purified by silica gel chromatography using an Isco automated flash chromatography system. The crude was dry loaded on to a 750 g pre-packed silica column adsorbed on to 170 g of celite. A linear gradient of 0 to 20% ethyl acetate in hexane was run over 16 column volumes. Removal of the solvent afforded 26 g of 26 as an off white foam (59% yield over 3 steps). $^1$H NMR ($CDCl_3$, 400 MHz) δ 7.79 (1H, brs), 7.49-7.46 (2H, m), 7.30-7.38 (3H, m), 7.09 (1H, s), 6.77 (1H, brs), 5.24 (2H, s), 3.91 (3H, s), 1.54 (9H, s), 1.41 (9H, s). $^{13}$C NMR ($CDCl_3$, 100 MHz) δ 160.9, 153.1, 149.9, 146.6, 136.0, 134.7, 131.5, 128.7, 128.6, 128.4, 127.8, 123.7, 114.6, 102.6, 85.6, 81.0, 71.1, 52.3, 28.5, 27.3. IR (neat) $v_{max}$ 3355, 2984, 2933, 1763, 1725, 1716, 1615, 1575, 1541, 1505, 1449, 1393, 1361, 1338, 1310, 1256, 1221, 1152, 1080, 980, 908, 878, 843, 817, 758, 723, 693 $cm^{-1}$. HRMS (ES+) calculated for $C_{27}H_{32}O_7N_2I$ $(M+H)^+$ 623.1249 found 623.1246.

To manufacture compound (27): 26 (26 g, 41.8 mmol) was dissolved in DMF (418 mL) and treated with t-BuOK (9.37 g, 84 mmol) and technical grade (90%) 1,3-dichloropropene as a mixture of cis and trans isomers (12.90 mL, 125 mmol). After stirring for 1.5 hours with the vessel submerged in a room temperature water bath, the reaction was cooled to 0° C. and quenched with saturated aqueous $NH_4CL$ (20 mL). The mixture was diluted with $Et_2O$ (1000 mL), and washed twice with of 50% saturated brine in water (1000 mL), and once with saturated brine (1000 mL). The $Et_2O$ was dried over $MgSO_4$, concentrated, and co-evaporated with DCM 6 times to afford a brown foam which was purified by silica gel chromatography using an Isco automated flash chromatography system. The crude was dry loaded on to a 220 g pre-packed silica column adsorbed on silica. A linear gradient of 0 to 10% ethyl acetate in hexane was run over 16 column volumes. Removal of the solvent afforded 18 g of 27 as a light brown foam (62% yield—mixture of E/Z isomers). $^1$H NMR ($CDCl_3$, 400 MHz, mixture of E/Z isomers) δ 7.28-7.44 (5H, m) 7.18 (1H, s), 6.65-6.47 (1H, m), 5.80-6.00 (2H, m]), 5.17-5.28 (2H, m), 4.46 & 4.18 (1H, m), 4.33 & 3.73 (1H, m), 3.93 (3H, s), 1.53 (9H, s), 1.29 & 1.27 (9H, s). $^{13}$C NMR ($CDCl_3$, 100 MHz) δ 160.9, 154.2, 150.0, 145.7, 138.7, 135.9, 132.2, 128.9, 128.4, 128.0, 127.5, 125.4, 121.8, 120.7, 115.3, 109.7 86.0, 83.9, 80.6, 70.7, 52.4, 49.5, 46.2, 28.4, 27.3. IR (neat) $v_{max}$ 2976, 2921, 1775, 1731, 1702, 1694, 1571, 1535, 1467, 1454, 1435, 1391, 1372, 1299, 1251, 1227, 1150, 1118, 1077, 978, 932, 885, 842, 829, 782, 764, 739, 731, 699 $cm^{-1}$. HRMS (ES+) calculated for $C_{30}H_{35}O_7N_2CII$ $(M+H)^+$ 697.1172 found 697.1174.

To manufacture compound (28): 27 (9 g, 12.9 mmol) was dissolved in anhydrous toluene and degassed with a stream of $N_2$ for 45 mins prior to addition of AIBN (0.530 g, 3.23 mmol) and TTMSS (4.38 mL, 14.20 mmol). The resulting solution was refluxed a 90° C. under $N_2$. After 1 hour the reaction was allowed to cool to room temperature before being concentrated and subjected directly to silica gel column chromatography using an Isco automated flash chromatography system. A 120 g pre-packed silica column was used, and 0% ethyl acetate in hexane run for 5 column volumes rising to 10% linearly over the subsequent 5 column volumes, holding at 10% until complete elution of the product. The reaction was repeated on the same scale and the products combined, affording 10.28 g of 28 as white foam (70% yield). $^1$H NMR (DMSO-D6, 400 MHz) δ 7.69 (1H brs), 7.47-7.29 (6H, m), 5.27 (2H, s), 4.13 (1H, t, J=9.7), 4.06-3.89 (4H, m), 3.87 (3H, s), 1.48 (9H, s), 1.39 (9H, s). $^{13}$C NMR (DMSO-D6, 100 MHz) δ 160.4, 151.4, 149.5, 145.1, 136.2, 128.4, 128.0, 127.9, 123.5, 113.2, 108.5, 97.4, 85.0, 80.3, 69.7, 52.3, 52.2, 47.6, 40.7 (obscured by DMSO peak observed by HSQC), 28.0, 26.8, 22.0. IR (neat) $v_{max}$ 3002, 2977, 2921, 2357, 1782, 1720, 1698, 1593, 1538, 1494, 1494, 1439, 1417, 1379, 1343, 1241, 1214, 1141, 1089, 1022, 988, 918, 899, 836, 765, 745, 712, 699, 691, 664 cm$^{-1}$. HRMS (ES+) calculated for $C_{30}H_{36}O_7N_2Cl$ (M+H)$^+$ 571.2206 found 571.2201.

To manufacture compound (29): 28 (10.28 g, 18.00 mmol) was dissolved in a mixture of THF (167 ml) and MeOH (111 ml) and treated with a saturated aqueous solution of LiOH (56 mL) drop wise. After 3 hours the THF and MeOH was removed under reduced pressure, and the residue diluted with water (100 mL). Acidification with 5 M HCl promoted the precipitation 29 as a white solid which was collected by filtration. Recovery from the filter by dissolution in ethyl acetate and co-evaporation with DCM afforded 10 g of 29 as a light green foam (100% yield). $^1$H NMR (DMSO-D6, 400 MHz) δ 13.43 (1H, brs), 7.69 (1H, brs), 7.49-7.29 (6H, m), 5.26 (2H, s), 4.13 (1H, t, J=9.7), 4.05-3.87 (4H, m), 1.49 (9H, s), 1.37 (9H, s). $^{13}$C NMR (DMSO-D6, 100 MHz) δ 161.5, 151.5, 149.1, 136.2, 129.5, 128.4, 128.0, 127.6, 123.6, 123.4, 122.4, 107.7 97.1, 84.6, 80.0, 69.7, 52.2, 47.6, 40.8 (obscured by DMSO peak observed by HSQC), 28.1, 26.8, 22.0. IR (neat) $v_{max}$ 2976, 2929, 2361, 2328, 1770, 1694, 1683, 1593, 1538, 1495, 1418, 1393, 1368, 1251, 1142, 1085, 1013, 978, 908, 942, 792, 745, 695, 668 cm$^{-1}$. HRMS (ES+) calculated for $C_{29}H_{34}O_7N_2Cl$ (M+H)$^+$ 557.2049 found 557.2044.

To manufacture the Fmoc protected compound (7): 29 (10 g, 17.95 mmol) was dissolved in 4 M HCl in dioxane (180 mL) and stirred at room temperature overnight. Following removal of the dioxane under reduced pressure, the residue was dissolved in THF (269 mL). The resulting solution was cooled to 0° C., before being treated with NaHCO$_3$ (4.52 g, 53.9 mmol) in water (90 mL), followed by Fmoc-Cl (4.64 g, 17.95 mmol) dropwise in THF (100 mL). After 5 min the reaction was quenched with MeOH (2 mL), and the THF and MeOH removed under reduced pressure. The remaining mixture was acidified with 2 M HCL, and extracted 3 times with 2-MeTHF, and dried over MgSO$_4$. Crude 7 was purified by silica gel chromatography using an Isco automated flash chromatography system. The crude was dry loaded on to a 220 g pre-packed silica column adsorbed on to 18 g of silica. A linear gradient of 0 to 5% MeOH in DCM was run. Removal of the solvent afforded 8.3 g of racemic 7 as a light green/brown foam (80% yield over 2 steps). $^1$H NMR (DMSO-D6, 400 MHz) δ 12.97 (1H, brs), 11.90 (1H, s), 7.90 (2H, d, J=6.7), 7.74-7.68 (2H, m), 7.67-7.57 (2H, m), 7.53-7.23 (8H, m), 7.20 (1H, d, J=1.8), 5.35-5.84 (2H, brs, [rotameric coalescence observed at 333K, δ 5.17, 2H, s]), 4.74-4.31 (3H, m, [rotameric coalescence observed at 333K, δ 4.55, 2H, app quin, δ 4.39, 1 H, t, J=6.6]), 4.23-4.14 (1H, m), 4.10-3.94 (3H, m), 3.93-3.84 (1H, m). $^{13}$C NMR (DMSO-D6, 100 MHz) δ 162.5, 152.0, 145.6, 143.8, 140.8, 136.8, 129.9, 128.2, 127.8, 127.6, 127.4, 127.2, 125.6, 125.1, 124.1, 120.2, 112.7, 105.8, 95.4, 69.5, 66.6, 51.9, 47.6, 46.7, 41.0, 34.4. IR (neat) $v_{max}$ 2950, 2367, 2320, 1694, 1682, 1593, 1538, 1441, 1404, 1318, 1247, 1218, 1171, 1131, 1085, 1018, 966, 903, 827, 737, 696, 667, 621 cm$^{-1}$. HRMS (ES−) calculated for $C_{34}H_{26}O_5N_2Cl$ (M−H)$^-$ 577.1536 found 577.1527.

Preparative chiral resolution of 7 was achieved using super critical fluid chromatography. Separation was affected using a Chiralpak AD-H column (250×30 mm, 5 micron), and an isocratic flow of 50% CO$_2$, and 50% IPA containing 0.1% TFA, at 45 mL per min. The back pressure was regulated at 10 MPa, and column temperature controlled at 40° C. A racemate of 7 (9.8 g) was dissolved in THF:MeOH 1:1 (100 mL), and 1.25 mL (125 mg) injected every 9 mins. Fractions were monitored by UV (220 nm), collected, combined and dried to afford 2.82 g of peak 1 (5.5 min), and 3.1 g of peak 2 (7 min), both as cream solids (α=1.27). Peak 1 $[α]_D$ −20 (c 0.05, DMF). Peak 2 $[α]_D$ +20 (c 0.05, DMF).

Analytical supercritical fluid chromatography of peak 1 showed a 7% impurity with similar retention time to peak 2. The mass of this peak suggested the loss of Cl as opposed to racemisation. NMR analysis showed no evidence of this impurity, with the H$^1$ NMR of both enantiomers being identical to that of the racemate, with the exception of a small amount of residue IPA.

Peak 1 was assigned as the natural enantiomer based on the sign of specific rotation matching that of the well characterised seco-Boc-DSA derivative (Boger, D. L.; Machiya, K.; Hertzog, D. L.; Kitos, P. A.; Holmes, D. *J. Am. Chem. Soc.* 1993, 115, 9025). Peak 1 $[α]_D$ −20° (c 0.05, DMF), Peak 2 $[α]_D$ +20° (c 0.05, DMF).

Example 2: Application of Fmoc-Protected Compound I to Solid Phase Peptide Synthesis A commercially available Wang supported alanine resin was prepared for coupling by swelling in DCM for 30 min, followed by DMF for a further 30 min. Subsequent treatment with 40% piperidine in DMF for 10 min, and 20% piperidine in DMF for 5 min twice, removed the alanine's Fmoc protection. A positive Kaiser Test confirmed the present of the free amine. The resin was then treated with a modest excess of the subunit 7 (see reaction scheme 1) (1.1 eq. based on the manufacture's resin loading) which had been pre-activated for 30 sec prior to addition, by treatment with an equimolar quantity of HBTU, and a twofold excess of both HOBt.H$_2$O and DIPEA in DMF. After two hours of shaking, the Kaiser test was repeated. A negative result was observed, and suggested complete coupling of subunit 7 to the Wang supported alanine. The resin was treated again with piperidine in DMF as previously described, affecting removal of Fmoc protection from the indoline nitrogen. This allowed coupling of a further alanine residue, using a fivefold excess of Fmoc-protected alanine for 45 minutes, which had been preactivated for 30 seconds with equimolar quantities of HBTU and HOBT.H$_2$O, and a twofold excess of DIPEA in DMF. The resin was then prepared for cleavage by removal of the final Fmoc group and extensive washing with DCM, followed by drying under a stream of N$_2$.

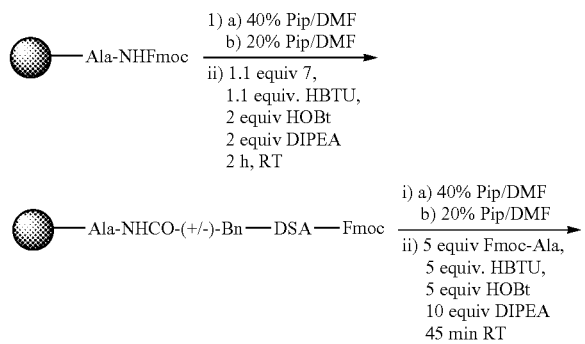

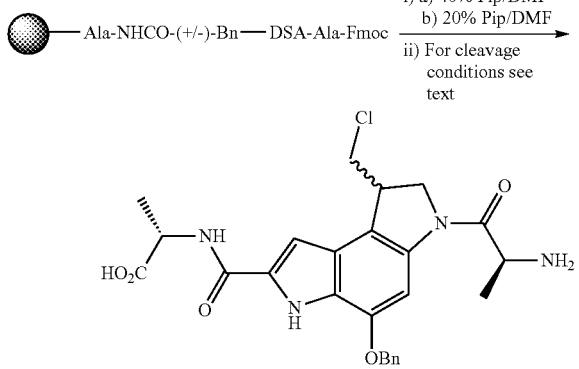

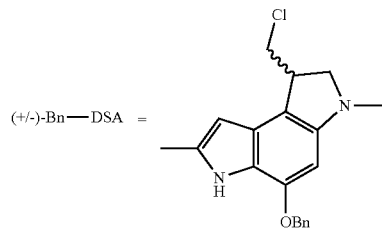

The resin was cleaved using standard conditions for peptide synthesis. The dried resin was treated with a solution of 95% TFA, 2.5% TIPS, and 2.5% H$_2$O for 2 hours. The cleavage mixture was filtered and concentrated, followed by precipitation with the addition of cold Et$_2$O.

Example 3: Qualitative Analysis of Resins and Coupling Reagents for Addition of the Subunit to the Solid Phase HPLC analysis of the crude product revealed the formation of several significant side products, shown in the graph of FIG. 3.

Figure 3:
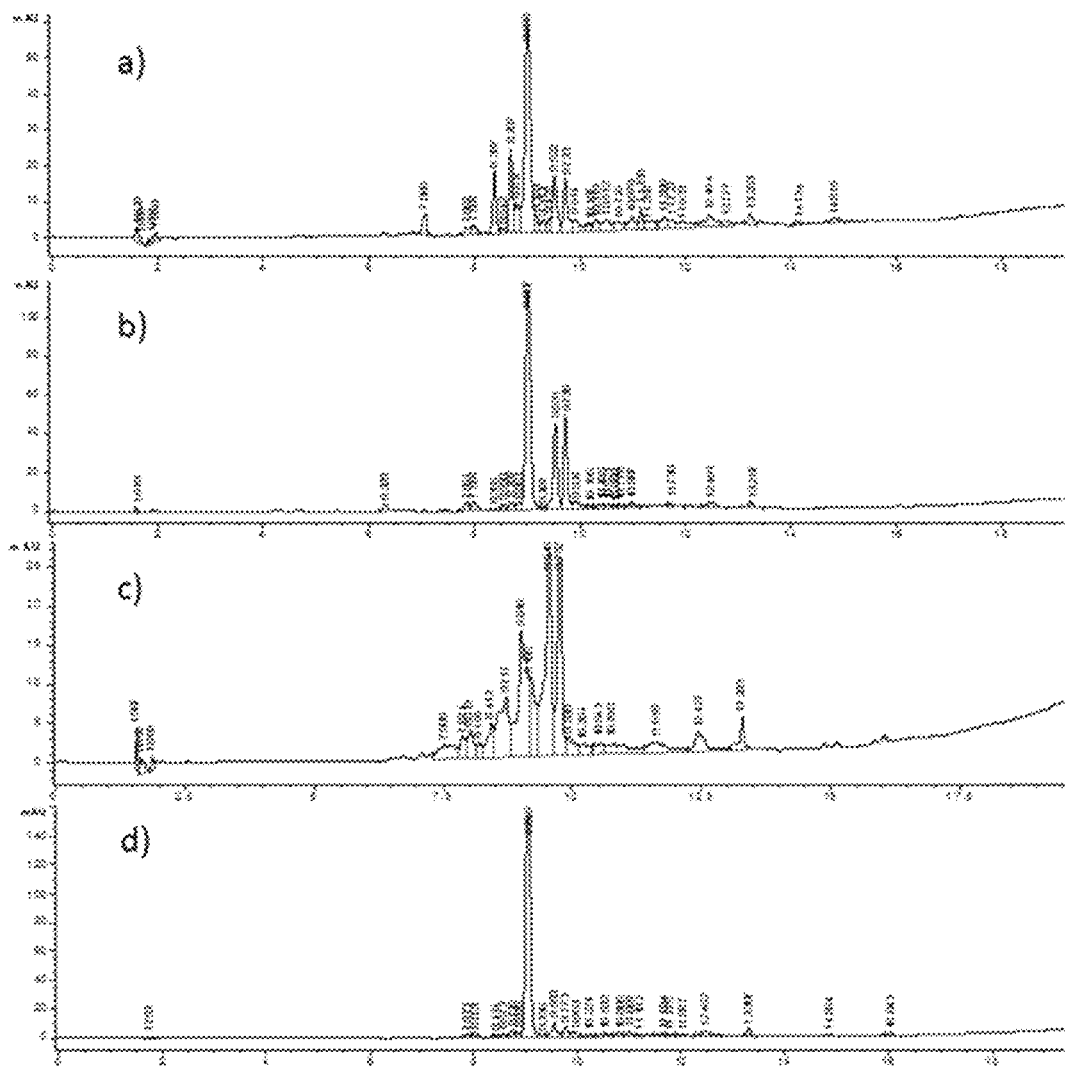
FIG. 3 is a graph showing HPLC analysis of the crude product revealed the formation of several significant side products. In particular, the graph shows HPLC analysis of crude HO-Ala-DSA-Ala-NH$_2$ after cleavage under varying conditions. a) 95% TFA, 2.5% TIPS, 2.5% H$_2$O. b) 50% TFA, 50% DCM. c) 95% TFA, 5% DCM. d) 47.5% TFA, 47.5% DCM, 2.5% TIPS, 2.5% H$_2$O. 10 mg of dried resin was cleaved under either conditions a, b, c, or d with 5 mL of the respective cleavage cocktail for 2 hours. The cleavage mixture was filtered and evaporated to dryness. The crude was dissolved in 1 mL of CH$_3$OH and analysed by HPLC at 254 nm. Agilent Eclipse XDB-C18 column, 4.8×150 mm, 5 uM. Solvent A: [Water and 0.05% TFA], Solvent B: [CH$_3$OH and 0.05% TFA]. Gradient: 0% [B] to 95% [B], from 0 min to 15 mins, 95% [B] to 0% [B] from 15 to 20 mins. Monitored UV 254 nM.

The graph of FIG. 3 shows HPLC analysis of crude HO-Ala-DSA-Ala-NH$_2$ after cleavage under varying conditions. a) 95% TFA, 2.5% TIPS, 2.5% H$_2$O. b) 50% TFA, 50% DCM. c) 95% TFA, 5% DCM. d) 47.5% TFA, 47.5% DCM, 2.5% TIPS, 2.5% H$_2$O. 10 mg of dried resin was cleaved under either conditions a, b, c, or d with 5 mL of the respective cleavage cocktail for 2 hours. The cleavage mixture was filtered and evaporated to dryness. The crude was dissolved in 1 mL of CH$_3$OH and analysed by HPLC at 254 nm. Agilent Eclipse XDB-C18 column, 4.8×150 mm, 5 uM. Solvent A: [Water and 0.05% TFA], Solvent B: [CH$_3$OH and 0.05% TFA]. Gradient: 0% [B] to 95% [B], from 0 min to 15 mins, 95% [B] to 0% [B] from 15 to 20 mins. Monitored UV 254 nM.

It was suspected that these products may have resulted from degradation during cleavage as opposed to representing problems during the synthesis. As a result the synthesis was repeated to allow optimisation of the cleavage conditions.

Figure 4:
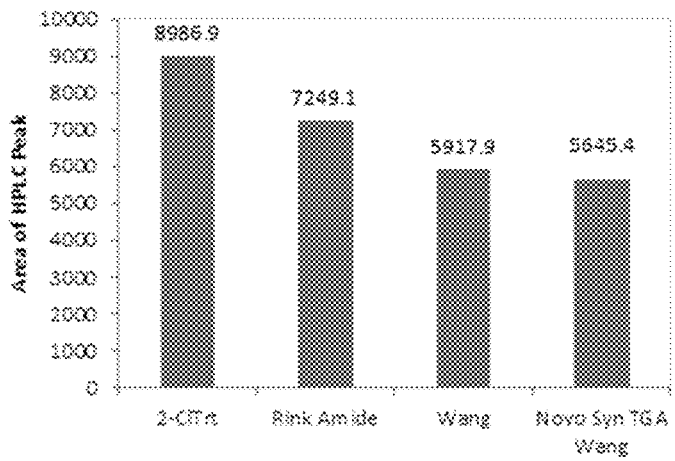
FIG. 4 shows HPLC Peak qualitative analysis of different resins (2Cl-Trt resin, Rink amide resin, Wang resin, and Novo Syn Wang) and coupling reagents for addition of 7 (Scheme 3) to the solid phase.
Figure 4:
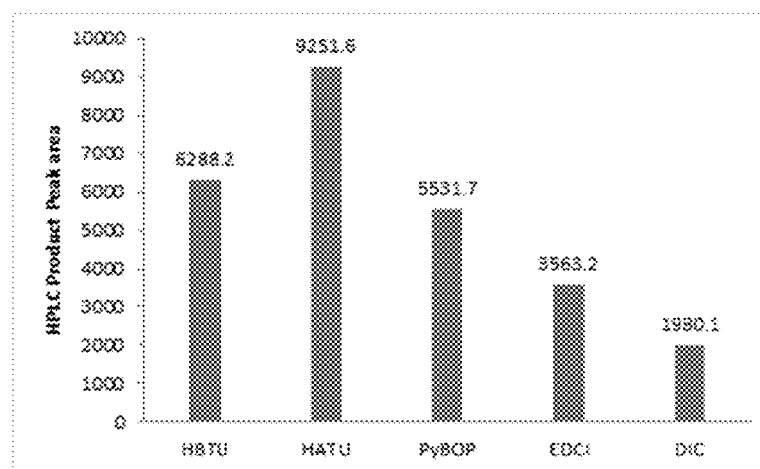

The dried resin was divided into 10 mg portions, and subjected to different cleavage conditions. The results of the HPLC analysis of the crude products are shown. Reducing the concentration of TFA to 50% in DCM and omission of the scavengers (TIPS, H$_2$O), led to a reduction in the number of side products (see conditions (b) versus (a) in graph of FIG. 3). However the product peak at 9 minutes was still accompanied by two significant side products at 9.5 and 9.7 minutes. Cleavage with 95% TFA and 5% DCM in the absence of scavengers (see (c) in graph of FIG. 3) led to almost complete absence of the product peak with the HPLC trace now being dominated by the side products at 9.5 and 9.7 minutes. Finally, reducing the concentration of TFA and including the scavengers (see graph of FIG. 3 (d)), 47.5% TFA, 47.5% DCM, 2.5% TIPS, 2.5% H$_2$O) produced an HPLC trace dominated by the product peak at 9 minutes. Mass spec analysis confirmed this peak to be the desired product. A qualitative analytical screen of other available resins was conducted. For these tests the C-terminal alanine was replaced with lysine and the indoline nitrogen capped with 5 equiv. of AcCl and 10 eq. of DIPEA in DMF for 45 minutes (see scheme 3 below and FIG. 4).

This synthesis was carried out on the same 0.038 mM scale with identical reaction times, on four different resins: 2Cl-Trt resin, Rink amide resin, Wang resin, and Novo Syn Wang resin. All were cleaved using 47.5% TFA, 47.5% DCM, 2.5% TIPS, 2.5% H$_2$O at the same volume for 2 hours. The crude cleavage mixtures were filtered, evaporated to dryness, and dissolved in the same volume of CH$_3$OH (1 mL) for HPLC analysis. The area of the product peak for each of the crudes was compared. The same volume of CH$_3$OH was used to dissolve the crudes, therefore the area of the peak doses give a qualitative indication of the quantity of product recovered from each resin. The best performing was 2-Cl-Trt resin, and Rink amide also performed well. 2-Cl-Trt resin can only be cleaved at the desired position, and the cation formed is more sterically hindered by the surrounding linker structure, making any potential back alkylation less likely. 2-Cl-Trt resin allowed cleavage with as little as 1% TFA. See FIG. 4.

Scheme 3: Qualitative analysis of the best resins and coupling reagents for addition of 7 to the solid phase.

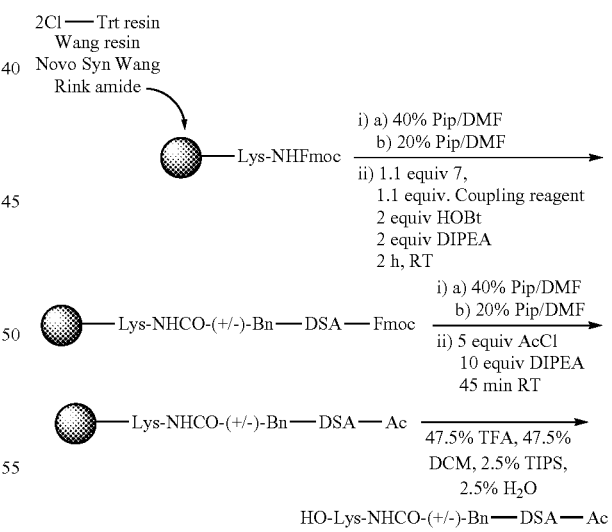

A similar test was used to compare available coupling reagents. The same analogue was synthesised at a 0.016 mM scale on 2-Cl-Trt resin. The only variation being the reagents used to couple subunit 7 to the resin-bound lysine. Again, a qualitative comparison of the area of the product peak on HPLC was carried out. HATU appeared to be the best performing coupling reagent followed by HBTU, PyBop, EDCl, and DIC.

Following these initial experiments, the natural enantiomer of 7, accessed from the large scale synthesis, was used to generate the library of analogues shown below:

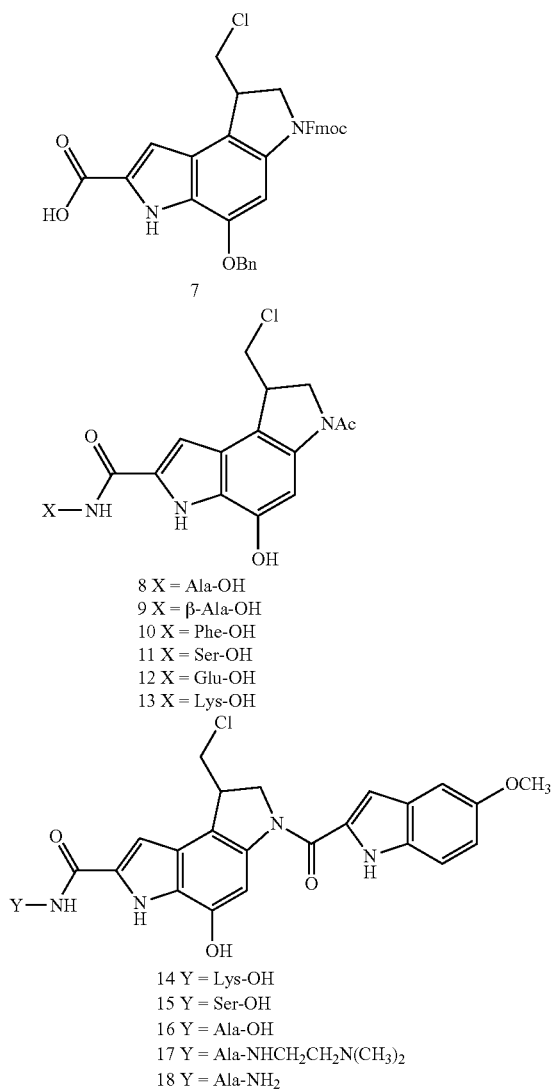

FIG. 1. Compounds 7-13 made in this study.

Full details of their synthesis and isolated yields are as follows:

(8): H-Ala-2Cltrt resin (53 mg, 0.039 mmol Ala, [manufacturer's resin loading 0.73 mmol/g]) was prepared for coupling by swelling in DCM for 30 mins followed by DMF for a further 30 mins. 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL) and 3 times with anhydrous DMF (10 mL). The resin was placed under an atmosphere of $N_2$ and treated with anhydrous DMF (2 mL), DIPEA (75 µL, 0.43 mmol), and AcCl (16 µL, 0.225 mmol). After 1 hour of shaking the resin was washed 6 times with DMF (10 mL) and 6 times with DCM. Cleavage was affected by addition of a solution of 1% TFA, 10% TIPS in DCM (10 mL). After 2 hours of shaking the cleavage mixture was filtered. The resin was rinsed 3 times with DCM (3 mL) and the combined filtrates were concentrated to dryness by rotary evaporation under vacuum. To ensure full recovery of the product the resin was soaked in THF:MeOH (10 mL), and after filtering this was combined with the rest of the cleavage product and again evaporated to dryness. The crude cleavage product was dissolved in THF:MeOH (2 mL) and treated with a slurry of 10% Pd/C (20 mg) in a 25% aqueous solution of ammonium formate (300 µL) under $N_2$. After 1 hour the Pd/C was removed by filtering through a plug of celite. Flash chromatography (silica gel, 7×1 cm, 0% to 30% MeOH in EtOAc) and trituration with hexane, afforded 10 mg of 8 as a beige solid (69% yield). $^1$H NMR (DMSO-D6, 400 MHz) δ 11.23 (1H, s), 9.70, (1H, s), 8.57 (1H, d, J=7.4), 7.70 (1H, s), 7.21 (1H, appt d, J=2.1), 4.44 (1H, appt quin, J=7.4), 4.33 (1H, appt t, J=11.7], 4.11-4.06 (1H, m), 4.04-3.96 (2H, m), 3.89-3.82 (1H, m), 2.15 (3H, s), 1.41 (3H, d, J=7.4). $^{13}$C NMR (observed by DEPT-ed-HSQC) (DMSO-D6, 100 MHz) δ 104.0 (CH1), 100.2 (CH1), 53.3 (CH2), 50.4 (CH1), 47.7 (CH2), 41.6 (CH1), 24.2 (CH3), 20.0 (CH3). HRMS (ES+) calculated for $C_{17}H_{19}ClN_3O_5$ $(M+H)^+$ 380.1008 found 380.1004.

(9): H-β-Ala-2Cltrt resin (53 mg, 0.039 mmol β-Ala, [manufacturer's resin loading 0.73 mmol/g]) was prepared for coupling by swelling in DCM for 30 mins followed by DMF for a further 30 mins. 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL) and 3 times with anhydrous DMF (10 mL). The resin was placed under an atmosphere of $N_2$ and treated with anhydrous DMF (2 mL), DIPEA (75 µL, 0.43 mmol), and AcCl (16 µL, 0.225 mmol). After 1 hour of shaking the resin was washed 6 times with DMF (10 mL) and 6 times with DCM. Cleavage was affected by addition of a solution of 1% TFA, 10% TIPS in DCM (10 mL). After 2 hours of shaking the cleavage mixture was filtered. The resin was rinsed 3 times with DCM (3 mL) and the combined filtrates were concentrated to dryness by rotary evaporation under vacuum. To ensure full recovery of the product the resin was soaked in MeOH (10 mL), and after filtering this was combined with the rest of the cleavage product and again evaporated to dryness. The crude cleavage product was dissolved in THF:MeOH (2 mL) and treated with a slurry of 10% Pd/C (20 mg) in a 25% aqueous solution of ammonium formate (300 µL) under $N_2$. After 1 hour the Pd/C was removed by filtering through a plug of celite. Flash chromatography (silica gel, 7×1 cm, 0% to 30% MeOH in EtOAc) and trituration with hexane afforded 12 mg of 9 as a beige solid (81% yield). $^1$H NMR (DMSO-D6, 400 MHz) δ 12.29 (1H, brs), 11.18 (1H, s), 9.69 (1H, s), 8.45 (1H, brs), 7.69 (1H, s), 7.11 (1H, s), 4.35-4.28 (1H, m), 4.07-3.95 (3H, m), 3.87-3.81 (1H, m), 3.48 (2H, obscured by $H_2O$ peak observed by HSQC and COSY), 2.53 (2H, obscured by DMSO peak observed by HSQC and COSY), 2.15 (3H, s). $^{13}$C NMR (observed by DEPT-ed-HSQC) (DMSO-D6, 100 MHz) δ 101.4 (CH1), 98.8 (CH1), 53.3 (CH2), 47.4 (CH2), 41.8 (CH1), 35.2 (CH2), 33.9 (CH2), 24.2 (CH3). HRMS (ES+) calculated for $C_{17}H_{19}ClN_3O_5$ $(M+H)^+$ 380.1008 found 380.1009.

(10): H-Phe-2Cltrt resin (53 mg, 0.039 mmol Phe, [manufacturer's resin loading 0.73 mmol/g]) was prepared for coupling by swelling in DCM for 30 mins followed by DMF for a further 30 mins. 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL) and 3 times with anhydrous DMF (10 mL). The resin was placed under an atmosphere of $N_2$ and treated with anhydrous DMF (2 mL), DIPEA (75 µL, 0.43 mmol), and AcCl (16 µL, 0.225 mmol). After 1 hour of shaking the resin was washed 6 times with DMF (10 mL) and 6 times with DCM. Cleavage was effected by addition of a solution of 1% TFA, 10% TIPS in DCM (10 mL). After 2 hours of shaking the cleavage mixture was filtered. The resin was rinsed 3 times with DCM (3 mL) and the combined filtrates were concentrated to dryness by rotary evaporation under vacuum. To ensure full recovery of the product the resin was soaked in THF:MeOH (10 mL), and after filtering this was combined with the rest of the cleavage product and again evaporated to dryness. The crude cleavage product was dissolved in THF:MeOH (2 mL) and treated with a slurry of 10% Pd/C (20 mg) in a 25% aqueous solution of ammonium formate (300 µL) under $N_2$. After 1 hour the Pd/C was removed by filtering through a plug of celite. Flash chromatography (silica gel, 7×1 cm, 0% to 10% MeOH in EtOAc) and trituration with hexane, afforded 11 mg of 10 as a beige solid (56% yield). $^1$H NMR (DMSO-D6, 400 MHz) δ 12.87 (1H, brs), 11.20 (1H, s), 9.70 (1H, s), 8.65 (1H, d, J=8.1), 7.70 (1H, s) 7.32-7.25 (4H, m), 7.21-7.16 (2H, m), 4.72-4.65 (1H, m), 4.36-4.27 (1H, m), 4.10-3.97 (3H, m), 3.89-3.82 (1H, m), 3.24-3.16 (1H, m), 3.06-2.98 (1H, m), 2.15 (3H, s). $^{13}$C NMR (observed by DEPT-ed-HSQC) (DMSO-D6, 100 MHz) δ 128.7 (CH1), 128 (CH1), 126.2 (CH1), 102.0 (CH1), 98.6 (CH1), 53.5 (CH1), 52.9 (CH2), 47.1 (CH2), 41.5 (CH1), 36.5 (CH2), 23.8 (CH3). HRMS (ES+) calculated for $C_{23}H_{23}O_5N_3Cl$ (M+H)$^+$ 456.1321 found 456.1317.

(11): H-Ser(tBu)-2Cltrt resin (51 mg, 0.039 mmol Ser, [manufacturer's resin loading 0.76 mmol/g]) was prepared for coupling by swelling in DCM for 30 mins followed by DMF for a further 30 mins. 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL) and 3 times with anhydrous DMF (10 mL). The resin was placed under an atmosphere of $N_2$ and treated with anhydrous DMF (2 mL), DIPEA (75 µL, 0.43 mmol), and AcCl (16 µL, 0.225 mmol). After 1 hour of shaking the resin was washed 6 times with DMF (10 mL) and 6 times with DCM. Cleavage was affected by addition of a solution of 20% TFA, 10% TIPS in DCM (10 mL). After shaking overnight the cleavage mixture was filtered. The resin was rinsed 3 times with DCM (3 mL) and the combined filtrates were concentrated to dryness by rotary evaporation under vacuum. To ensure full recovery of the product the resin was soaked in THF:MeOH (10 mL), and after filtering this was combined with the rest of the cleavage product and again evaporated to dryness. The crude cleavage product was dissolved in THF:MeOH (2 mL) and treated with a slurry of 10% Pd/C (20 mg) in a 25% aqueous solution of ammonium formate (300 µL) under $N_2$. After 1 hour the Pd/C was removed by filtering through a plug of celite. Preparative HPLC (see general Prep HPLC method) and lyophilization, afforded 7.5 mg of 11 as a beige solid (48% yield). $^1$H NMR (DMSO-D6, 400 MHz) δ 12.76 (1H, brs), 11.35 (1H, s), 9.72 (1H, s), 8.49 (1H, d, J=8.3), 7.71 (1H, s), 7.24 (1H, s), 5.01 (1H, brs), 4.58-4.48 (1H, m), 4.37-4.28 (1H, m), 4.14-3.97 (3H, m), 3.90-3.76 (3H, m), 2.15 (3H, s). $^{13}$C NMR (observed by DEPT-ed-HSQC) (DMSO-D6, 100 MHz) δ 102.0 (CH1), 98.3 (CH1), 61.0 (CH2), 55.0 (CH1), 53.0 (CH2), 47.2 (CH2), 41.6 (CH1), 23.8 (CH3). HRMS (ES+) calculated for $C_{17}H_{19}ClN_3O_6$ (M+H)$^+$ 396.0957 found 396.0956.

(12): H-Glu(OtBu)-2Cltrt resin (59 mg, 0.039 mmol Glu, [manufacturer's resin loading 0.65 mmol/g]) was prepared for coupling by swelling in DCM for 30 mins followed by DMF for a further 30 mins. 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL) and 3 times with anhydrous DMF (10 mL). The resin was placed under an atmosphere of $N_2$ and treated with anhydrous DMF (2 mL), DIPEA (75 µL, 0.43 mmol), and AcCl (16 µL, 0.225 mmol). After 1 hour of shaking the resin was washed 6 times with DMF (10 mL) and 6 times with DCM. Cleavage was affected by addition of a solution of 10% TFA, 10% TIPS in DCM (10 mL). After shaking for 6 hours the cleavage mixture was filtered. The resin was rinsed 3 times with DCM (3 mL) and the combined filtrates were concentrated to dryness by rotary evaporation under vacuum. To ensure full recovery of the product the resin was soaked in THF:MeOH (10 mL), and after filtering this was combined with the rest of the cleavage product and again evaporated to dryness. The crude cleavage product was dissolved in THF:MeOH (2 mL) and treated with a slurry of 10% Pd/C (20 mg) in a 25% aqueous solution ammonium formate (300 µL) under $N_2$. After 1 hour the Pd/C was removed by filtering through a plug of celite. Preparative HPLC (see general Prep HPLC method) and lyophilization, afforded 6.5 mg of 12 as a beige solid (38% yield). $^1$H NMR (DMSO-D6, 400 MHz) δ 12.51 (2H, brs), 11.25 (1H, s), 9.73 (1H, s), 8.52 (1H, brs), 7.70 (1H, s), 7.21 (1H, s), 4.49-4.30 (2H, m), 4.18-3.93 (3H, m), 3.91-3.80 (1H, m), 2.43-2.35 (2H, m), 2.21-2.04 (4H, m), 1.97-1.86 (1H, m). $^{13}$C NMR (observed by DEPT-ed-HSQC) (DMSO-D6, 100 MHz) δ 102.2 (CH1), 98.8 (CH1), 53.1 (CH2), 51.3 (CH1), 47.2 (CH2), 41.7 (CH1), 30.1 (CH2), 26.1 (CH2), 23.9 (CH3). HRMS (ES+) calculated for $C_{19}H_{21}ClN_3O_7$ 438.1063 (M+H)$^+$ found 438.1053.

(13): H-Lys(Boc)-2Cltrt resin (53 mg, 0.039 mmol Lys, [manufacturer's resin loading 0.73 mmol/g]) was prepared for coupling by swelling in DCM for 30 mins followed by DMF for a further 30 mins. 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL) and 3 times with anhydrous DMF (10 mL). The resin was placed under an atmosphere of $N_2$ and treated with anhydrous DMF (2 mL), DIPEA (75 µL, 0.43 mmol), and AcCl (16 µL, 0.225 mmol). After 1 hour of shaking the resin was washed 6 times with DMF (10 mL) and 6 times with DCM. Cleavage was affected by addition of a solution of 10% TFA, 10% TIPS in DCM (10 mL). After shaking for 2 hours the cleavage mixture was filtered. The resin was rinsed 3 times with DCM (3 mL) and the combined filtrates were concentrated to dryness by rotary evaporation under vacuum. To ensure full recovery of the product the resin was soaked in THF:MeOH (10 mL), and after filtering this was combined with the rest of the cleavage product and again evaporated to dryness. The crude cleavage product was dissolved in THF:MeOH (2 mL) and treated with a slurry of 10% Pd/C (20 mg) in a 25% aqueous solution ammonium formate (300 µL) under $N_2$. After 1 hour the Pd/C was removed by filtering through a plug of celite. Preparative HPLC (see general Prep HPLC method) and lyophilization, afforded 3.3 mg of 13 as a beige solid (19% yield). $^1$H NMR (DMSO-D6, 400 MHz) δ 12.79 (1H brs), 11.28 (1H, s), 9.79 (1H, s), 8.54 (1H, d, J=8.3), 7.73-7.69 (2H, brs), 7.71 (1H, s), 7.22 (1H, s), 4.46-4.38 (1H, m), 4.37-4.28 (1H, m), 4.14-3.95 (3H, m), 3.91-3.83 (1H, m), 2.82-2.76 (2H, m), 2.16 (3H, s), 1.86-1.74 (2H, m), 1.60-1.54 (2H, m), 1.47-1.41 (2H m). $^{13}$C NMR (observed by DEPT-ed-HSQC) (DMSO-D6, 100 MHz) δ 102.2 (CH1), 98.8 (CH1), 53.0 (CH2), 51.6 (CH1), 47.2 (CH2), 41.5 (CH1), 38.4 (CH2), 30.3 (CH2), 26.3 (CH2), 24.0 (CH3), 22.5 (CH2). HRMS (ES+) calculated for $C_{20}H_{26}ClN_4O_5$ 437.1586 (M+H)$^+$ found 437.1593.

(14): H-Lys(Boc)-2Cltrt resin (53 mg, 0.039 mmol Lys, [manufacturer's resin loading 0.73 mmol/g]) was prepared for coupling by swelling in DCM for 30 mins followed by DMF for a further 30 mins. 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL). 5-methoxyindole-2-carboxylic acid (38 mg, 0.199 mmol) was dissolved in 2 mL of DMF and treated with HATU (73 mg, 0.191 mmol) and DIPEA (70 µL, 0.401 mmol). After 10 secs the resulting solution was added to the resin and the mixture shaken overnight. The resin was washed 6 times with DMF (10 mL) and 6 times with DCM. Cleavage was affected by addition of a solution of 10% TFA, 10% TIPS in DCM (10 mL). After shaking for 2 hours the cleavage mixture was filtered. The resin was rinsed 3 times with DCM (3 mL) and the combined filtrates were concentrated to dryness by rotary evaporation under vacuum. To ensure full recovery of the product the resin was soaked in THF:MeOH (10 mL), and after filtering this was combined with the rest of the cleavage product and again evaporated to dryness. The crude cleavage product was dissolved in THF:MeOH (2 mL) and treated with a slurry of 10% Pd/C (30 mg) in a 25% aqueous solution ammonium formate (500 µL) under $N_2$. After 1 hour the Pd/C was removed by filtering through a plug of celite. Preparative HPLC (see general Prep HPLC method) and lyophilization, afforded 4.4 mg of 14 as a beige solid (20% yield). $^1$H NMR (DMSO-D6, 400 MHz) δ 11.56, (1H, s), 11.38 (1H, brs), 9.89 (1H, brs), 8.59 (1H brs), 7.76 (1H, brs), 7.59 (2H brs), 7.38 (1H, d, J=8.9), 7.26 (1H, s), 7.15 (1H, d, J=2.2), 7.02 (1H, d, J=1.4), 6.89 (1H, dd, J=8.9, 2.2), 4.82-4.67 (1H, m), 4.51-4.39 (2H, m), 4.18-4.03 (2H, m), 3.99-3.91 (1H, m), 3.78 (3H, s), 2.84-2.75 (2H, m), 1.92-1.74 (2H, m), 1.64-1.55 (2H, m), 1.49-1.42 (2H, m). $^{13}$C NMR (observed by DEPT-ed-HSQC) (DMSO-D6, 100 MHz) δ 114.8 (CH1), 112.8 (CH1), 104.5 (CH1), 102.4 (CH1), 101.8 (CH1), 99.5 (CH1), 54.9 (CH3), 54.4 (CH2), 51.8 (CH1), 47.1 (CH2), 42.0 (CH1), 38.4 (CH2), 3.3 (CH2), 26.4 (CH2), 22.4 (CH2). HRMS (ES+) calculated for $C_{28}H_{31}ClN_5O_6$ 568.1957 (M+H)$^+$ found 568.1949.

(15): H-Ser(tBu)-2Cltrt resin (56 mg, 0.039 mmol Lys, [manufacturer's resin loading 0.76 mmol/g]) was prepared for coupling by swelling in DCM for 30 mins followed by DMF for a further 30 mins. 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL). 5-methoxyindole-2-carboxylic acid (38 mg, 0.199 mmol) was dissolved in 2 mL of DMF and treated with HATU (73 mg, 0.191 mmol) and DIPEA (70 µL, 0.401 mmol). After 10 secs the resulting solution was added to the resin and the mixture shaken overnight. The resin was washed 6 times with DMF (10 mL) and 6 times with DCM. Cleavage was affected by addition of a solution of 20% TFA, 10% TIPS in DCM (10 mL). After shaking overnight the cleavage mixture was filtered. The resin was rinsed 3 times with DCM (3 mL) and the combined filtrates were concentrated to dryness by rotary evaporation under vacuum. To ensure full recovery of the product the resin was soaked in THF:MeOH (10 mL), and after filtering this was combined with the rest of the cleavage product and again evaporated to dryness. The crude cleavage product was dissolved in THF:MeOH (2 mL) and treated with a slurry of 10% Pd/C (20 mg) in a 25% aqueous solution of ammonium formate (300 µL) under $N_2$. After 1 hour the Pd/C was removed by filtering through a plug of celite. Preparative HPLC (see general Prep HPLC method) and lyophilization, afforded 3.3 mg of 15 as a beige solid (16% yield). $^1$H NMR (DMSO-D6, 400 MHz) δ 11.54 (1H, s), 11.43 (1H, s), 9.80 (1H, s), 8.52 (1H, d, J=7.4), 7.77 (1H, brs), 7.38 (1H, d, J=8.6), 7.29 (1H, d, J=1.4), 7.15 (1H, d, J=2.3), 7.02 (1H, d, J=1.3), 7.89 (1H, dd, J=8.6, 2.3), 4.79-4.71 (1H, m), 4.57-4.50 (1H, m), 4.47-4.37 (1H, m), 4.17-4.04 (2H, m), 3.99-3.89 (1H, m), 3.82-3.76 (2H, m), 3.78 (3H, s). $^{13}$C NMR (observed by DEPT-ed-HSQC) (DMSO-D6, 100 MHz) δ 114.6 (CH1), 112.8 (CH1), 104.2 (CH1), 102.4 (CH1), 101.7 (CH1), 99.5 (CH1), 61.1 (CH2), 55.0 (CH3), 54.8 (CH1), 54.4 (CH2), 47.0 (CH2), 42.0 (CH1). HRMS (ES−) calculated for $C_{25}H_{22}ClN_4O_7$ 525.1182 (M−H)$^-$ found 525.1187.

(16): H-Ala-2Cltrt resin (58 mg, 0.039 mmol Ala, [manufacturer's resin loading 0.72 mmol/g]) was prepared for coupling by swelling in DCM for 30 mins followed by DMF for a further 30 mins. 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL). 5-methoxyindole-2-carboxylic acid (38 mg, 0.199 mmol) was dissolved in 2 mL of DMF and treated with HATU (73 mg, 0.191 mmol) and DIPEA (70 µL, 0.401 mmol). After 10 secs the resulting solution was added to the resin and the mixture shaken overnight. The resin was washed 6 times with DMF (10 mL) and 6 times with DCM. Cleavage was affected by addition of a solution of 1% TFA, 10% TIPS in DCM (10 mL). After shaking for 2 hours the cleavage mixture was filtered. The resin was rinsed 3 times with DCM (3 mL) and the combined filtrates were concentrated to dryness by rotary evaporation under vacuum. To ensure full recovery of the product the resin was soaked in THF:MeOH (10 mL), and after filtering this was combined with the rest of the cleavage product and again evaporated to dryness. The crude cleavage product was dissolved in THF:MeOH (2 mL) and treated with a slurry of 10% Pd/C (20 mg) in a 25% aqueous solution ammonium formate (300 µL) under $N_2$. After 1 hour the Pd/C was removed by filtering through a plug of celite. Reverse phase flash chromatography (see general reverse phase flash chromatography method) and lyophilization, afforded 7 mg of 16 as a beige solid (35% yield). $^1$H NMR (DMSO-D6, 400 MHz) δ 12.67 (1H, Brs), 11.5 (1H, s), 11.32 (1H, s), 9.82 (1H, s), 8.62, (1H, d, J=7.0), 7.76 (1H, brs), 7.38 (1H, d, J=8.9), 7.27 (1H, s), 7.15 (1H, s), 7.02 (1H, s), 6.89 (1H, d, J=8.9), 4.81-4.71 (1H, m), 4.50-4.39 (2H, m), 4.16-4.06 (2H, m), 3.98-3.91 (1H, m), 3.78 (3H, s), 1.42 (3H, d, J=7.3). $^{13}$C NMR (observed by DEPT-ed-HSQC) (DMSO-D6, 100 MHz) δ 114.7 (CH1), 112.7 (CH1), 104.4 (CH1), 102.2 (CH1), 101.8 (CH1), 99.5 (CH1), 54.9 (CH3), 54.4 (CH2), 47.5 (CH1), 46.9 (CH2), 42.0 (CH1), 16.9 (CH3). HRMS (ES−) calculated for $C_{25}H_{22}ClN_4O_6$ 509.1233 (M−H)⁻ found 509.1234.

(17): H-Ala-2Cltrt resin (58 mg, 0.039 mmol Ala, [manufacturer's resin loading 0.72 mmol/g]) was prepared for coupling by swelling in DCM for 30 mins followed by DMF for a further 30 mins. 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL). 5-methoxyindole-2-carboxylic acid (38 mg, 0.199 mmol) was dissolved in 2 mL of DMF and treated with HATU (73 mg, 0.191 mmol) and DIPEA (70 µL, 0.401 mmol). After 10 secs the resulting solution was added to the resin and the mixture shaken overnight. The resin was washed 6 times with DMF (10 mL) and 6 times with DCM (10 mL). Cleavage was affected by addition of a solution of 1% TFA, 10% TIPS in DCM (10 mL). After shaking for 2 hours the cleavage mixture was filtered. The resin was rinsed 3 times with DCM (3 mL) and the combined filtrates were concentrated to dryness by rotary evaporation under vacuum. To ensure full recovery of the product the resin was soaked in THF:MeOH (10 mL), and after filtering this was combined with the rest of the cleavage product and again evaporated to dryness. The crude was dissolved in DMF (1 mL), and treated with HATU (16 mg, 0.042 mmol), and DIPEA (20 µL, 0.12 mmol). After 10 secs the resulting solution was treated with 3-(Dimethylamino)-1-propylamine (30 µL, 0.24 mmol) and stirred at room temperature for 2 hours, prior to precipitation with cold $H_2O$ (15 mL), and collection by centrifusion. The precipate was dissolved in THF:MeOH (2 mL) and treated with a slurry of 10% Pd/C (20 mg) in a 25% aqueous solution ammonium formate (300 µL) under $N_2$. After 1 hour the Pd/C was removed by filtering through a plug of celite. Reverse phase flash chromatography (see general reverse phase flash chromatography method) and lyophilization, afforded 4 mg of 17 as a beige solid (17% yield). $^1$H NMR (DMSO-D6, 400 MHz) δ 11.54 (1H, s), 11.37 (1H, s), 9.91 (1H, s), 9.33 (1H, brs), 8.56 (1H, appt t, J=7.3), 8.21 (1H, appt q, J=5.6), 7.79 (1H, brs), 7.39 (1H, d, J=8.7), 7.28 (1H, s), 7.16 (1H, d, J=2.3), 7.03 (1H, s), 6.90 (1H, dd, J=8.7, 2.3), 4.81-4.72 (1H, m), 4.47-4.39 (2H, m), 4.16-4.08 (2H, m), 3.99-3.91 (1H, m), 3.78 (3H, s), 3.21-3.12 (2H, m), 3.08-2.99 (2H, m), 2.76 (6H, s), 1.84-1.75 (2H, m), 1.38 (3H, d, J=7.1). $^{13}$C NMR (observed by DEPT-ed-HSQC) (DMSO-D6, 100 MHz) δ 114.8 (CH1), 112.8 (CH1), 104.4 (CH1), 102.6 (CH1), 101.8 (CH1), 99.4 (CH1), 54.9 (CH3), 54.5 (CH2), 54.3 (CH2), 48.7 (CH1), 47.1 (CH2), 42.2 (CH3), 42.0 (CH1), 35.2 (CH2), 24.1 (CH2), 17.6 (CH3). HRMS (ES+) calculated for $C_{30}H_{36}ClN_6O_5$ 595.2430 (M+H)⁺ found 595.2418.

(18): Rink amide MBHA resin (107 mg, 0.039 mmol, [manufacturer's resin loading 0.36 mmol/g]) was prepared for coupling by swelling in DCM for 30 mins followed by DMF for a further 30 mins, and treatment with piperidine in DMF (3 mL 40% 10 mins, 3 mL 20% 5 mins twice). The resin was washed 6 times with DMF (10 mL). Fmoc-Ala-OH (121 mg, 0.39 mmol), was dissolved in 2 mL of DMF and treated with HBTU (133 mg, 0.39 mmol), HOBt.$H_2O$ (54 mg, 0.39 mmol) and DIPEA (135 µL, 0.78 mmol). After 30 secs the solution was added to the resin and shaken for 45 mins. The coupling was repeated and the resin washed 6 times with DMF (10 mL) prior to Fmoc deprotection with piperidine in DMF (3 mL 40% 10 mins, 3 mL 20% 5 mins twice). Following Fmoc deprotection the resin was wash a further 6 times with DMF (10 mL). 7 (25 mg, 0.043 mmol) was dissolved in 2 mL of DMF and treated with HATU (13 mg, 0.043 mmol) and DIPEA (16 µL, 0.086 mmol). After 10 secs the resulting solution was added to the resin and the mixture shaken overnight. The resin was washed 6 times with DMF (10 mL) and removal of the Fmoc protection of the indoline nitrogen affected with piperidine in DMF (3 mL 40% 10 mins, 3 mL 20% 5 mins twice). Following Fmoc deprotection the resin was washed 6 times with DMF (10 mL). 5-methoxyindole-2-carboxylic acid (38 mg, 0.199 mmol) was dissolved in 2 mL of DMF and treated with HATU (73 mg, 0.191 mmol) and DIPEA (70 µL, 0.401 mmol). After 10 secs the resulting solution was added to the resin and the mixture shaken overnight. The resin was washed 6 times with DMF (10 mL) and 6 times with DCM. Cleavage was affected by addition of a solution of 47% TFA, 47% DCM, 3% TIPS and 3% $H_2O$ (10 mL). After shaking for 2 hours the cleavage mixture was filtered. The resin was rinsed 3 times with DCM (3 mL) and the combined filtrates were concentrated to dryness by rotary evaporation under vacuum. The crude cleavage product was dissolved in THF:MeOH (2 mL) and treated with a slurry of 10% Pd/C (20 mg) in a 25% aqueous solution of ammonium formate (300 µL) under $N_2$. After 1 hour the Pd/C was removed by filtering through a plug of celite. Flash chromatography (silica gel, 7×1 cm, 10% MeOH in DCM) and trituration with hexane, afforded 6.8 mg of 18 as a beige solid (34% yield). $^1$H NMR (DMSO-D6, 400 MHz) δ 11.54 (1H, s), 11.35 (1H, s), 9.82 (1H, s), 8.46 (1H, d, J=7.6), 7.76 (1H, brs), 7.47 (1H, brs), 7.38 (1H, d, J=8.9), 7.27 (1H, d, J=2.0), 7.15 (1H, d, J=2.3), 7.04 (1H, brs), 7.02 (1H, s), 6.89 (1H, dd, J=8.9, 2.3), 4.80-4.72 (1H, m), 4.51-4.40 (2H, m), 4.16-4.06 (2H, m), 3.98-3.89 (1H, m), 3.78 (3H, s), 1.35 (3H, d, J=7.1). $^{13}$C NMR (observed by DEPT-ed-HSQC) (DMSO-D6, 100 MHz) δ 114.7 (CH1), 112.8 (CH1), 104.4 (CH1), 102.3 (CH1), 101.8 (CH1), 99.3 (CH1), 54.9 (CH3), 54.4 (CH2), 48.0 (CH1), 47.1 (CH2), 41.9 (CH1) 18.0

(CH3). HRMS (ES+) calculated for $C_{25}H_{25}ClN_5O_5$ 510.1539 (M+H)$^+$ found 510.1533.

All analogues where synthesised on 2-Cl-Trt resin, with the exception of 18, where Rink amide was employed to provide a neutral terminal amide after cleavage. When using 2-Cl-Trt resin, the cleavage concentration of TFA was reduced further to 1% for analogues not requiring t-butyl side chain deprotection, increasing to 10 or 20% and extended reaction times for those that did. When the TFA concentration was reduced to this level, $H_2O$ no longer served as an effective scavenger, presumably as it was not miscible with the larger volumes of dichloromethane now being used. This was resolved by increasing the concentration of TIPS to 10%. Interestingly, if 10% $H_2O$ was also included, t-butyl side chain deprotection did not occur.

The benzyl protecting group was removed via transfer hydrogenation using Pd—C/$HCO_2NH_4$ on crude cleavage products, and the active compounds purified by either preparative reverse phase HPLC, or silica gel Flash chromatography, depending on the polarity of the side chain.

The highest yield and optimum purity of the target compound was obtained when the reaction was carefully carried out and quenched after 1 hour.

Example 4: DNA Alkylation Studies

DNA alkylation studies were performed for all compounds produced in example 3:

Controls 30 and 31 were synthesised as follows:

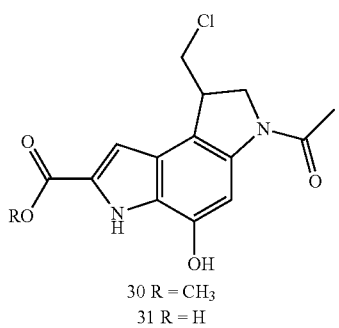

30 R = CH$_3$
31 R = H

Synthesis of compound (30): compound 28 (50 mg, 0.087 mmol) was dissolved in 4 M HCl in EtOAc (5 mL) containing TIPS (500 µL) and the solution was stirred overnight at room temperature. After removal of the solvent under reduced pressure, the residue was taken up in DMF (7 mL), and cooled to 0° C. The solution was treated with DIPEA (30 µL, 0.17 mmol), and AcCl (6 µL, 0.087 mmol) and stirred under $N_2$. After 2 hours the reaction was poured over crushed ice and the product was collected as a beige precipitate. This was dissolved in a 1:1 mixture of THF and MeOH (2 mL) and added to a suspension of 10% Pd/C (20 mg) in 25% aqueous ammonium formate (300 µL) under $N_2$. After 1 hour, the reaction was filtered through celite. Flash chromatography (silica gel, 7×1 cm, 5% MeOH in DCM) afforded 17 mg 31 as a white solid (60% yield over 3 steps). $^1$H NMR (DMSO-D6, 400 MHz) δ 11.55 (1H, brs), 9.72 (1H, s), 7.75 (1H, s), 7.22 (1H, app d, J=2.10), 4.31 (1H, t, J=11.6), 4.10-3.96 (3H, m), 3.91-3.87 (1H, m), 3.85 (3H, s), 2.15 (3H, s). $^{13}$C NMR (DMSO-D6, 100 MHz) δ 167.4, 161.4, 143.6, 138.0, 127.7, 125.4, 124.0, 111.7, 106.0, 99.7, 53.2, 51.8, 47.7, 41.5, 24.1. HRMS (ES+) calculated for $C_{15}H_{16}ClN_2O_4$ (M+H)$^+$ 323.0793 found 323.0797.

Synthesis of compound (31): compound 30 (57 mg, 0.14 mmol) was dissolved in a 3:2:1 mixture of THF:MeOH:$H_2O$ (6 mL), and treated with LiOH.$H_2O$ (110 mg, 2.62 mmol) overnight at room temperature. The organic solvents were removed under reduced pressure, and the residue diluted with 1 M HCl (10 mL). The mixture was cooled to 4° C. for 72 hrs, and the product was collected as a beige precipitate by centrifugation. This was dissolved in a 1:1 mixture of THF and MeOH (2 mL) and added to a suspension of 10% Pd/C (20 mg) in 25% aqueous ammonium formate (300 µL) under $N_2$. After 1 hour the reaction was filtered through celite and the crude purified by preparative HPLC. Lyophilization afforded 6.5 mg of 31 as a tan solid (15% yield over 2 steps). $^1$H NMR (DMSO-D6, 400 MHz) δ 12.92 (1H, brs), 11.33 (1H, s), 9.62 (1H, s), 7.72 (1H, s), 7.13 (1H, s), 4.37-4.25 (1H, m), 4.12-3.95 (3H, m), 3.92-3.81 (1H, m), 2.15 (3H, s). $^{13}$C NMR (DMSO-D6, 100 MHz) δ 167.4, 162.5, 143.5, 137.9, 129.1, 125.1, 124.1, 111.6, 105.6, 99.5, 53.2, 47.7, 41.5, 24.1. HRMS (ES+) calculated for $C_{14}H_{14}ClN_2O_4$ (M+H)$^+$ 309.0637 found 309.0637.

Figure 2:
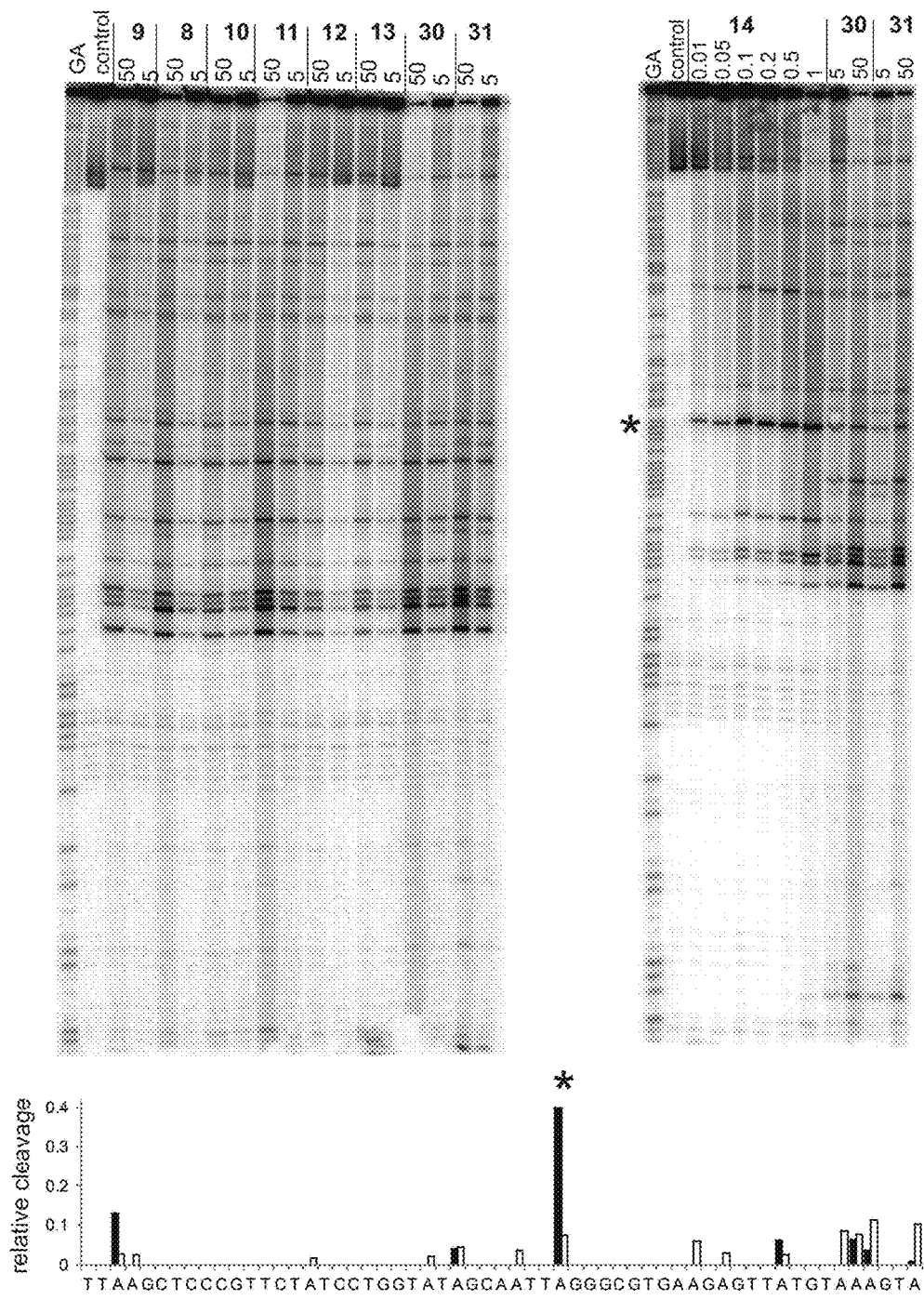
FIG. 2 shows the results of DNA alkylation studies. In particular, the figure shows DNA cleavage of DNA fragment MS1 by duocarmycin derivatives. Left hand panel compounds 9-13 and control compounds 30 and 31. Right hand panel 14, compared with compounds 30 and 31. Tracks labelled GA are sequence markers for purines; control is DNA in the absence of added ligand. Ligand concentrations (μM) are indicated at the top of each gel lane. The lower panel shows the relative cleavage at each position for 14 (filled bars) and 31 (open bars). The asterisk indicates the location of the best cleavage with 14.

DNA alkylation studies were performed as follows: The MS1 DNA fragment was prepared and labeled as previously described by Lavesa M; Fox K. R. *Analytical Biochemistry* (2001), 293, 246-250 by cleaving the parent plasmid with HindIII and SacI and labelling the 3'-end of the HindIII site with α-$^{32}$P[dATP] using Klenow fragment (exo−). 1.5 µL of each compound (diluted in 10 mM Tris-HCl pH 7.5, containing 10 mM NaCl) was incubated with 1.5 µL of the radiolabelled DNA and incubated overnight at 37° C. The samples were then mixed with an equal volume of formamide containing 10 mM EDTA and ligand specific cleavage was induced by heating at 100° C. for 3 minutes. Samples were loaded onto 8% denaturing polyacrylamide gels containing 8M urea. The dried gel was exposed to a phosphorimager screen and analysed using a Typhoon phosphorimager. The results are shown in FIG. 2.

The results show that the sequence selectivity of compounds 8-13 closely matches that for the controls 30 and 31 (which were analysed as the racemic mixtures) with little evidence for sequence selectivity other than the alkylation of an A in short AT runs as shown in the open bars in the lower panel.

The presence of significant cleavage for compound 31 suggests that the presence of a carboxylic acid does not affect the DNA alkylating ability of the subunit, as the reactivity of 31 closely matches that for 30. The extended agent 14, which is more similar in structure to the full natural product duocarmycin SA than to the simple alkylation subunit, displayed significantly enhanced DNA alkylation activity compared with the other compounds (see results, right hand panel) producing cleavage products at much lower concentrations. 14 reacted predominantly with As at the 3'-end of AT sequences, with fewer cleavage sites than the other compounds. The major cleavage on this fragment is observed at AATTA, (see results, asterisk) demonstrating a sequence selectivity that is closer to that expected for the natural product. The enhancement of the alkylation seen with 14 compared with 13 was significant with clear alkylation at 10 nM compared with 5 µM for the latter.

Example 5: Measuring Antiproliferative Activity

Antiproliferative activity was determined by MTS assay (Howell L A, Bowater R A, O'Connell M A, Reszka A P, Neidle S, Searcey M. (2012) Synthesis of Small Molecules Targeting Multiple DNA Structures using Click Chemistry. *ChemMedChem*, 7, 792-804) using the CellTiter 96 Aq$_{ueous}$ One Solution Cell Proliferation Assay (Promega) and following the manufacturer's instructions.

The HL60 cell line was purchased from ECACC (Porton Down, UK). Cells were cultured in RPMI 1640 medium supplemented with 10% foetal calf serum and 2 mM L-glutamine. HL-60 cells were passaged twice weekly and maintained between $1-9\times10^5$ cells/ml at 37° C. and 5% $CO_2$.

HL-60 cells ($3\times10^4/100$ μl) were seeded in 96-well plates and left untreated or treated with DMSO (vehicle control), duocarmycins, or doxorubicin hydrochloride at 8 concentrations (see below) in triplicate for 72 hr at 37° C. with 5% $CO_2$. Following this, MTS assay reagent was added for 4 hrs and the absorbance measured at 490 nm using the Polarstar Optima microplate reader (BMG Labtech). $IC_{50}$ values were calculated using GraphPad Prism Version 5.0 software.

The following concentrations were tested: Compounds 8, 9, 10, 11, 12, 13, 14, 15, 30, and 31, (500 μM, 250 μM, 100 μM, 10 μM, 1 μM, 0.1 μM, 0.01 μM, 0.001 μM); Compounds 16, 17, 18, and doxorubicin (100 μM, 10 μM, 1 μM, 0.1 μM, 0.01 μM, 0.001 μM, 0.0001 μM, 0.00001 μM).

The results are shown in table 1:

TABLE 1

Antiproliferative activity of the duocarmycin compounds.

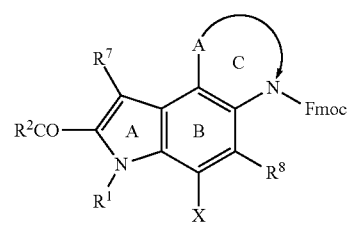

| | $R_1$ | $R_2$ | $IC_{50}$ (μM) |
|---|---|---|---|
| 8 | CO-Ala-OH | Ac | 85 |
| 9 | CO-β-Ala-OH | Ac | >300 |
| 10 | CO-Phe-OH | Ac | 32 |
| 11 | CO-Ser-OH | Ac | 40 |
| 12 | CO-Glu-OH | Ac | 286 |
| 13 | CO-Lys-OH | Ac | >300 |
| 14 | CO-Lys-OH | 5-MeOInd | 0.374 |
| 15 | CO-Ser-OH | 5-MeOInd | 0.153 |
| 16 | CO-Ala-OH | 5-MeOInd | 0.038 |
| 17 | CO-Ala-NH($CH_2$)$_2$N($CH_3$)$_2$ | 5-MeOInd | 0.064 |
| 18 | CO-Ala-$NH_2$ | 5-MeOInd | 0.028 |
| 30 | $COOCH_3$ | Ac | 0.025 |
| 31 | COOH | Ac | >300 |
| Doxorubicin (+ve control) | | | 0.125 |

Activity was assessed in HL60 human leukaemia cell lines and was measured using the MTS assay.
For details, see the experimental section.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of general formula I

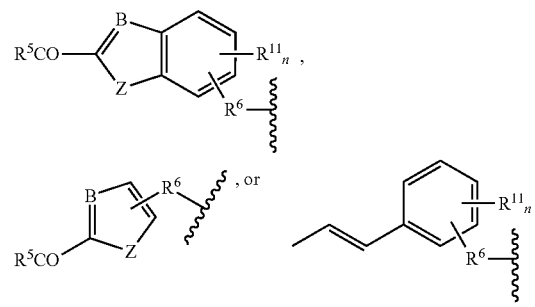

wherein

A is $CH(CH_2Y)CH_2$ or $CH_2CH(Y)CH_2$;

Y is a leaving group selected from the group consisting of $OCOOR^{15}$, $OCONHR^{16}$, Cl, Br, I, and $OSOOR^{17}$, wherein $R^{15}$ is selected from the group consisting of $C_{1-4}$ alkyl, optionally substituted phenyl, $C_{7-12}$-aralkyl and optionally substituted heteroaryl; $R^{16}$ is selected from the group consisting of $C_{1-4}$ alkyl, optionally substituted phenyl, $C_{7-12}$-aralkyl and optionally substituted heteroaryl; and $R^{17}$ is selected from the group consisting of $C_{1-4}$ alkyl, optionally substituted phenyl, $C_{7-12}$-aralkyl and optionally substituted heteroaryl;

$R^1$ is H, $C_{1-6}$ alkyl, or tertiary butyloxycarbonyl (BOC);

$R^2$ is OH, $OR^3$, $SR^{10}$, $N(R^4)_2$, or a carboxylic acid activating group;

$R^3$ is $C_{1-6}$ alkyl, $C_{5-24}$ aryl, heteroaryl or $C_{1-6}$ substituted alkyl;

each $R^4$ is independently selected from H, $C_{1-6}$ alkyl, $C_{5-24}$ aryl, heteroaryl, $C_{1-6}$ substituted alkyl, the C-terminal residue of an amino acid, C-terminal peptide of a solid phase peptide-synthetic substrate group optionally linked to a SPPS substrate, and $Ar^1$;

where $Ar^1$ is selected from

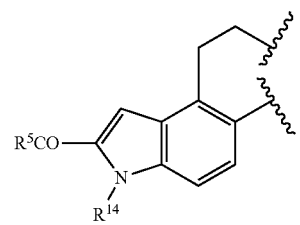

or two $R^4$'s together represent

X is OH or $OR^9$;

$R^7$ and $R^8$ are independently selected from H, $C_{1-4}$ alkyl, OH, $C_{1-4}$ alkoxy, $C_{1-6}$ alkyl, CN, Cl, Br, I and $NO_2$;

33 each $R^5$ is OH, $OR^3$, $SR^{10}$, $N(R^6)_2$, or a carboxylic acid activating group;

each $R^6$ is a bond, a $C_{1-6}$ alkanediyl, a $C_{6-24}$ arylene, a $C_{6-24}$ alkarylene, a heteroarylene or heteroaryl-alkylene;

Z is O, S, —CH═CH or $NR^{14}$;

B is N or CH;

each $R^{11}$ is independently selected from H, $C_{1-4}$ alkyl, OH, $C_{1-4}$ alkoxy, $C_{1-6}$ alkyl, CN, Cl, Br, I and $NO_2$;

n is 0-4;

$R^9$ is $C_{1-6}$ alkyl, $C_{5-24}$ aryl, heteroaryl, $C_{1-6}$ substituted alkyl or a phenol protecting group;

$R^{10}$ is H, $C_{1-6}$ alkyl, $C_{5-24}$ aryl, heteroaryl or $C_{1-6}$ substituted alkyl;

and $R^{14}$ is H, $C_{1-6}$ alkyl or an amine protecting group.

2. A method of synthesising an amide compound by the following steps:

a) deprotecting a compound of the formula I by removing the FMOC group to leave a free secondary amine group-containing intermediate

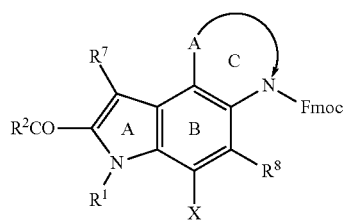

I wherein

A is $CH(CH_2Y) CH_2$ or $CH_2CH(Y)CH_2$;

Y is a leaving group selected from the group consisting of $OCOOR^{15}$, $OCONHR^{16}$, Cl, Br, I, and $OSOOR^{17}$, wherein $R^{15}$ is selected from the group consisting of $C_{1-4}$ alkyl, optionally substituted phenyl, $C_{7-12}$-aralkyl and optionally substituted heteroaryl; $R^{16}$ is selected from the group consisting of $C_{1-4}$ alkyl, optionally substituted phenyl, $C_{7-12}$-aralkyl and optionally substituted heteroaryl; and $R^{17}$ is selected from the group consisting of $C_{1-4}$ alkyl, optionally substituted phenyl, $C_{7-12}$-aralkyl and optionally substituted heteroaryl;

$R^1$ is H, $C_{1-6}$ alkyl, or BOC;

$R^2$ is OH, $OR^3$, $SR^{10}$, $N(R^4)_2$, or a carboxylic acid activating group;

$R^3$ is $C_{1-6}$ alkyl, $C_{5-24}$ aryl, heteroaryl, or $C_{1-6}$ substituted alkyl;

each $R^4$ is independently selected from H, $C_{1-6}$ alkyl, $C_{5-24}$ aryl, heteroaryl, $C_{1-6}$ substituted alkyl; the C-terminal residue of an amino acid, C-terminal peptide of a solid phase peptide-synthetic substrate group optionally linked to a SPPS substrate, and $Ar^1$;

where $Ar^1$ is selected from

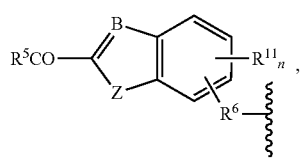

34

-continued

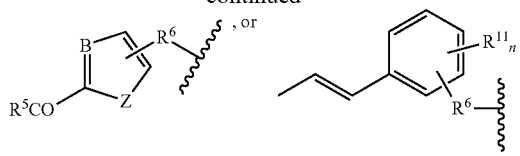

or two $R^4$'s together represent

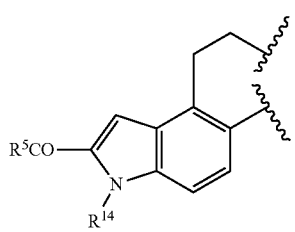

X is OH or $OR^9$;

$R^7$ and $R^8$ are independently selected from H, $C_{1-4}$ alkyl, OH, $C_{1-4}$ alkoxy, $C_{1-6}$ alkyl, CN, Cl, Br, I and $NO_2$;

each $R^5$ is OH, $OR^3$, $SR^{10}$, $N(R^6)_2$, or a carboxylic acid activating group;

each $R^6$ is a bond, a $C_{1-6}$ alkanediyl, a $C_{6-24}$ arylene, a $C_{6-24}$ alkarylene, a heteroarylene or heteroaryl-alkylene;

Z is O, S, —CH═CH or $NR^{14}$;

B is N or CH;

each $R^{11}$ is independently selected from H, $C_{1-4}$ alkyl, OH, $C_{1-4}$ alkoxy, $C_{1-6}$ alkyl, CN, Cl, Br, I and $NO_2$;

n is 0-4;

$R^9$ is $C_{1-6}$ alkyl, $C_{5-24}$ aryl, heteroaryl, $C_{1-6}$ substituted alkyl or a phenol protecting group;

$R^{10}$ is H, $C_{1-6}$ alkyl, $C_{5-24}$ aryl, heteroaryl or $C_{1-6}$ substituted alkyl;

and $R^{14}$ is H, $C_{1-6}$ alkyl or an amine protecting group;

b) contacting the amine intermediate with a carboxylate reagent of the formula II

 II where $R^{12}$ is OH or a carboxylic acid activating group;

$R^{13}$ is $C_{1-6}$ alkyl, $C_{5-24}$ aryl, heteroaryl or $C_{1-6}$ substituted alkyl, any of which may be substituted by a targeting ligand or a cytotoxic moiety or $Ar^2$ or $R^{13}$ is

where $R^{18}$ is the side chain of a natural or non-natural alpha amino acid; a targeting ligand or a cytotoxic moiety;

$Ar^2$ is selected from:

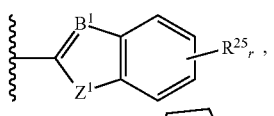

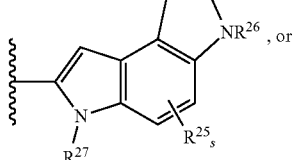

$Z^1$ is O, S, —CH=CH— or $NR^{27}$;
$B^1$ is N or CH;
s is 0, 1 or 2;
r is 0-4;
$R^{26}$ is selected from H, $CONH_2$, acyl, FMOC, $C_{1-6}$ alkyl, $C_{5-24}$ aryl, heteroaryl, $C_{1-6}$ substituted alkyl, C-terminal peptide and $Ar^2$; and
the or each $R^{25}$ is independently selected from $C_{1-6}$ alkyl, OH, $C_{1-6}$ alkoxy, $C_{1-6}$ alkylthio, CN, Cl, Br, I and $NO_2$ and $—R^{29}NHCOR^{28}$;
$R^{29}$ is a bond, a $C_{1-6}$ alkanediyl, a $C_{6-24}$ arylene, a $C_{6-24}$ alkarylene, a heteroarylene or heteroaryl-alkylene;
$R^{28}$ is a $C_{1-6}$ alkyl, $C_{6-24}$ aryl, $C_{5-24}$ aralkyl, heteroaryl or $C_{1-6}$ substituted alkyl;
$R^{27}$ is a $C_{1-6}$ alkyl or BOC
to form the amide compound.

3. The method according to claim 2, wherein $R^{13}$ is $Ar^2$ and $Ar^2$ is a group of formula:

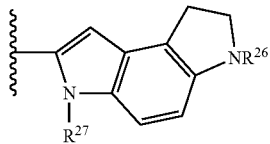

wherein $R^{27}$ is BOC and $R^{26}$ is FMOC.

4. The method according to claim 2, wherein $R^{13}$ is $Ar^2$ and $Ar^2$ is a group of formula:

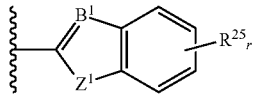

wherein r is 1-3 and the or each $R^{25}$ is independently selected from OH, $C_{1-6}$ alkyl, $C_{1-6}$ alkoxy and $C_{1-6}$ alkylthio.

5. The method according to claim 2, wherein $R^{13}$ is FMOC—NH—CH($R^{18}$) where $R^{18}$ is the side chain of a natural alpha amino acid.

6. The method according to claim 3, further comprising the step:
c) removing the second FMOC group to leave a free amine group.

7. The method according to claim 5, further comprising the step:
c) removing the second FMOC group to leave a free amine group.

8. The method according to claim 7, further comprising the step:
d) carrying out a further step b as defined in claim 1 with a second carboxylate reagent of formula II wherein $R^{13}$ is FMOC N—CH($R^{18}$)— where $R^{18}$ is the side chain of a natural or non-natural alpha amino acid; or $R^{13}$ is an alkyl or aryl group substituted by a targeting ligand or a cytotoxic moiety.

9. The method according to claim 2, wherein in the compound of the formula I $R^2$ is $N(R^4)_2$, where one of the groups $R^4$ is the C-terminal residue of an amino acid, a C-terminal peptidyl group or a solid phase peptide synthetic substrate linking group linked to SPPS-substrate.

10. The method according to claim 9, comprising the preliminary steps of synthesising the compound of formula I by reacting a compound of general formula III

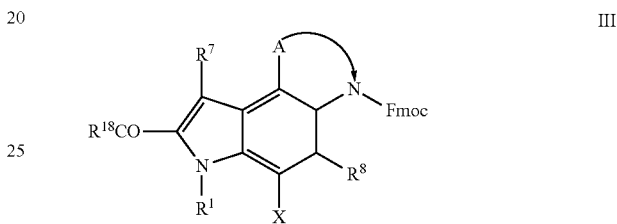

wherein A, $R^8$, X, $R^1$ and $R^7$ have the same meanings as in claim 1, and $R^{18}$ is OH or a carboxylic acid activating group
with a compound of formula IV $$R^{20}NHR^{19} \quad [IV]$$

where $R^{19}$ is H or $C_{1-6}$ alkyl,
and $R^{20}$ is $C_{1-6}$ alkyl, $C_{5-24}$ aryl, heteroaryl, $C_{1-6}$ substituted alkyl or CH($R^{18}$) $COR^{21}$ where $R^{18}$ is the side chain of a natural or non-natural amino acid and $R^{21}$ is a carboxylic acid protecting group or a C-terminal peptidyl moiety or a linker group of a SPPS substrate;
or $R^{19}$ and $R^{20}$ are linked to form a saturated or unsaturated 5 or 6 membered heterocyclic ring.

11. The method according to claim 10, wherein in the compound of the formula IV $R^{20}$ is CH($R^{18}$)$COR^{21}$ wherein $R^{21}$ is a linker group of a SPPS substrate.

12. The method according to claim 11, wherein $R^{21}$ is a peptidyl linker linked to a chlorotrityl resin, preferably a LINK-amide resin.

* * * * *